US006804385B2

(12) United States Patent
Eisfeld et al.

(10) Patent No.: US 6,804,385 B2
(45) Date of Patent: Oct. 12, 2004

(54) METHOD AND DEVICE FOR SELECTIVELY TARGETING CELLS WITHIN A THREE-DIMENSIONAL SPECIMEN

(75) Inventors: Timothy M. Eisfeld, San Diego, CA (US); Manfred R. Koller, San Diego, CA (US); Bernhard O. Palsson, La Jolla, CA (US)

(73) Assignee: Oncosis, San Diego, CA (US)

( * ) Notice: Subject to any disclaimer, the term of this patent is extended or adjusted under 35 U.S.C. 154(b) by 254 days.

(21) Appl. No.: 10/037,478

(22) Filed: Oct. 24, 2001

(65) Prior Publication Data

US 2002/0177885 A1 Nov. 28, 2002

Related U.S. Application Data

(60) Provisional application No. 60/243,015, filed on Oct. 24, 2000.

(51) Int. Cl.[7] ................................................ G06K 9/00
(52) U.S. Cl. ...................................... 382/128; 359/368
(58) Field of Search ................................ 382/128–134, 382/100, 255, 275, 291, 312; 210/695; 250/302; 356/436; 359/368; 378/43, 133; 435/6, 7–92; 436/514; 600/420

(56) References Cited

U.S. PATENT DOCUMENTS

| | | | | |
|---|---|---|---|---|
| 3,864,571 A | * | 2/1975 | Stillman et al. ............. 250/302 |
| 4,284,897 A | | 8/1981 | Sawamura et al. ....... 250/461.2 |
| 4,395,397 A | | 7/1983 | Shapiro ...................... 424/577 |
| 4,532,402 A | | 7/1985 | Overbeck .............. 219/121.78 |
| 4,629,687 A | | 12/1986 | Schindler et al. .............. 435/4 |
| 5,013,460 A | | 5/1991 | Kasuya et al. ............ 435/460 |
| 5,035,693 A | | 7/1991 | Kratzer et al. ................ 606/12 |
| 5,072,382 A | * | 12/1991 | Kamentsky .................. 382/133 |
| 5,109,276 A | | 4/1992 | Nudelman et al. ............ 358/88 |
| 5,235,522 A | | 8/1993 | Bacus ........................ 364/497 |
| 5,287,272 A | | 2/1994 | Rutenberg et al. ..... 364/413.01 |
| 5,296,963 A | | 3/1994 | Murakami et al. .......... 359/389 |
| 5,381,224 A | | 1/1995 | Dixon et al. .................. 356/72 |
| 5,428,690 A | | 6/1995 | Bacus et al. ................. 382/128 |
| 5,432,865 A | | 7/1995 | Kasdan et al. .............. 382/128 |
| 5,552,605 A | * | 9/1996 | Arata ..................... 250/363.04 |
| 5,590,168 A | * | 12/1996 | Iketaki ......................... 378/43 |
| 5,646,411 A | | 7/1997 | Kain et al. ................ 250/458.1 |
| 5,672,880 A | | 9/1997 | Kain .......................... 250/235 |
| 5,690,846 A | | 11/1997 | Okada et al. .......... 219/121.78 |
| 5,713,364 A | * | 2/1998 | DeBaryshe et al. ......... 600/476 |
| 5,719,391 A | | 2/1998 | Kain .......................... 250/235 |
| 5,732,150 A | | 3/1998 | Zhou et al. ................. 382/133 |
| 5,784,162 A | | 7/1998 | Cabib et al. ................. 356/346 |
| 5,790,710 A | | 8/1998 | Price et al. ................. 382/255 |
| 5,795,755 A | | 8/1998 | Lemelson ................ 435/173.5 |
| 5,828,776 A | | 10/1998 | Lee et al. .................... 382/133 |
| 5,891,656 A | * | 4/1999 | Zarling et al. ............. 435/7.92 |
| 5,932,872 A | | 8/1999 | Price ........................ 250/201.3 |
| 5,995,143 A | | 11/1999 | Price et al. .................. 348/345 |
| 6,099,522 A | | 8/2000 | Knopp et al. ................. 606/10 |
| 6,166,385 A | | 12/2000 | Webb et al. ............. 250/458.1 |

OTHER PUBLICATIONS

Gazitt et al., "Purified CD34$^+$Lin$^-$Thy$^+$ Stem Cells Do Not Contain Clonal Myeloma Cells," *Blood*, 86(1):381–389 (1995).

Grate and Wilson, "Laser–Mediated, Site–Specific Inactivation of RNA Transcripts," *Proc. Natl. Acad. Sci.*, 96:6131–6136 (1999).

(List continued on next page.)

*Primary Examiner*—Jayanti K. Patel
(74) *Attorney, Agent, or Firm*—McDermott Will & Emery LLP

(57) ABSTRACT

The invention provides an apparatus for electromagnetically affecting a particle of interest in a specimen. The apparatus includes (a) a stage capable of supporting the specimen; (b) a detector including at least one camera, wherein the detector is capable of resolving a particle of interest within the specimen; (c) a means for locating the particle of interest in three dimensions; (d) a means for focusing electromagnetic radiation to a focal volume within the specimen; and (e) a means for adjusting the relative positions of the stage and electromagnetic radiation focusing means, thereby positioning the particle of interest within the focal volume.

152 Claims, 9 Drawing Sheets

OTHER PUBLICATIONS

Gribben et al., "Immunologic Purging of Marrow Assessed by PCR Before Autologous Bone Marrow Transplantation for B–Cell Lymphoma," *New Engl. J. Med.*, 325(22):1525–1533 (1991).

Gulliya and Pervaiz, "Elimination of Clonogenic Tumor Cells from HL–60, Daudi, and U–937 Cell Lines by Laser Photoraditation Therapy: Implications for Autologous Bone Marrow Purging," *Blood*, 73(4):1059–1065 (1989).

Jay, "Selective Destruction of Protein Function by Chromophore–Assisted Laser Inactivation," *Proc. Natl. Acad. Sci.*, 85:5454–5458 (1988).

Mapara et al., "monitoring of Tumor Cell Purging After Highly Efficient Immunomagnetic Selection of CD34 Cells from Leukapheresis Products in Breast Cancer Patients: Comparison of Immunocytochemical Tumor Cell Staining and Reverse Transcriptase—Polymerase Chain Reaction," *Blood*, 89(1):337–344 (1997).

Mapara et al., "Combined Positive/Negative Purging and Transplantation of Peripheral Blood Progenitor Cell Autografts in Breast Cancer Patients: A Pilot Study," *Exper. Hemat.*, 27:169–175 (1999).

Oleinick and Evans, "The Photobiology of Photodynamic Therapy: Cellular Targets and Mechanisms," *Rad. Res.*, 150:S146–S156 (1998).

Palumbo et al., "Targeted Gene Transfer in Eucaryotic Cells by Dye–Assisted Laser Optoporation," *J. Photochem. Photobiol. B: Biol.*, 36:41–46 (1996).

Paulus et al., "Combined Positive/Negative Selection for Highly Effective Purging of PBPC Grafts: Towards Clinical Application in Patients with B–CLL," *Bone Marr. Transplan.*, 20:415–420 (1997).

Robertson et al., "Human Bone Marrow Depleted of CD33–Positive Cells Mediates Delayed but Durable Reconstitution of Hematopoiesis: Clinical Trial of MY9 Monoclonal Antibody–Purged Autografts for the Treatment of Acute Myeloid Leukemia," *Blood*, 79(9):2229–2236 (1992).

Theriot and Mitchison, "Comparison of Actin and Cell Surface Dynamics in Motile Fibtoblasts," *J. Cell Biol.*, 119(2):367–377 (1992).

Tricot et al., $CD34^+THY^+LIN^-$ Peripheral Blood Stem Cells (PBSC) Effect Timely Trilineage Engraftment in Multiple Myeloma (MM), *Blood*, 86:293a, Abstract 1160 (1995).

Wagner et al., "Isolation of Small, Primitive Human Hematopoietic Stem Cells: Distribution of Cell Surface Cytokine Receptors and Growth in SCID–Hu Mice," *Blood*, 86(2):512–523 (1995).

Bird et al., "4–Hydroperoxycyclophosphamide Purged Autologous Bone Marrow Transplantation in Non–Hodgkin's Lymphoma Patients at High Risk of Bone Marrow Involvement," *Bone Marr. Transplan.*, 18:309–313 (1996).

Clarke et al., "A Recombinant Bcl–$X_s$ Adenovirus Selectively Induces Apoptosis in Cancer Cells but Not in Normal Bone Marrow Cells," *Proc. Natl. Acad. Sci.*, 92:11024–11028 (1995).

Denk, "Two–Photon Scanning Photochemical Microscopy: Mapping Ligand–Gated Ion Channel Distributions," *Proc. Natl. Acad. Sci.*, 91:6629–6633 (1994).

Dooley et al., "A Novel, Inexpensive Technique for the Removal of Breast Cancer Cells from Mobilized Peripheral Blood Stem Cell Products," *Blood*, 88:252a, Abstract 995 (1996).

* cited by examiner

METHOD AND DEVICE FOR SELECTIVELY TARGETING CELLS WITHIN A THREE-DIMENSIONAL SPECIMEN

This application claims benefit of provisional application serial No. 60/243,015, filed Oct. 24, 2000, and is hereby incorporated by reference.

BACKGROUND OF THE INVENTION

This invention relates to methods and devices for selectively identifying and individually manipulating particles in mixtures and more specifically to methods and devices for selectively removing unwanted target cells from a tissue with an energy beam.

Previous methods of removing target cells from tissues have been developed based upon the ability to effectively separate target cells from the tissue or availability of toxic chemical agents that are delivered specifically to the target cells. Effective separation of target cells is difficult to achieve due to the difficult balance to be struck between providing conditions that are rigorous enough to remove target cells from their native tissues and gentle enough not to damage other cells desired to be maintained in the tissue. Furthermore, many of the separation methods require extensive disruption of the tissue thereby precluding or rendering difficult reconstitution of viable tissue with the remaining cells. Although, toxic agents can be delivered to the target cells while still in the tissue, the degree of specificity required to prevent collateral damage to surrounding tissue is often difficult to achieve.

Thus, there is a need for apparatus and methods for rapidly and efficiently identifying and targeting particular cells within complex populations found in biological tissues. The present invention satisfies this need and provides related advantages as well.

SUMMARY OF THE INVENTION

The invention provides an apparatus for electromagnetically affecting a particle of interest in a specimen. The apparatus includes (a) a stage capable of supporting the specimen; (b) a detector including at least one camera, wherein the detector is capable of resolving a particle of interest within the specimen; (c) a means for locating the particle of interest in three dimensions; (d) a means for focusing electromagnetic radiation to a focal volume within the specimen; and (e) a means for adjusting the relative positions of the stage and electromagnetic radiation focusing means, thereby positioning the particle of interest within the focal volume.

The invention further provides a method for electromagnetically affecting a particle of interest in a specimen. The method includes the steps of (a) obtaining a plurality of nonidentical two-dimensional sectional representations of the specimen in which the particle of interest is discernable in at least one of the sectional representations; (b) combining the plurality of sectional two-dimensional representations to produce a three-dimensional representation of the specimen; (c) locating the particle of interest in three dimensions based on the three-dimensional representation; and (d) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

Further provided is a method for electromagnetically affecting a particle of interest in a specimen. The method includes the steps of (a) focusing a plurality of detectors on a plurality of focal planar regions in a specimen; (b) obtaining a plurality of two-dimensional sectional representations each corresponding to one of the focal planar regions, wherein a particle of interest can be discerned in at least one of the two-dimensional sectional representations; (c) storing the plurality of two-dimensional sectional representations in a computer memory; (d) combining the plurality of two-dimensional sectional representations to produce a three-dimensional representation of at least a portion of the specimen; (e) locating the particle of interest in the specimen based on the three-dimensional representation of at least a portion of the specimen; and (f) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

The invention also provides a method for electromagnetically affecting a particle of interest in a specimen. The method includes the steps of: (a) obtaining a plurality of two-dimensional sectional representations of the specimen at different Z-levels, wherein the particle of interest is discernable in at least one of the sectional representations; (b) selecting a two-dimensional sectional representation from the plurality of two-dimensional sectional representations wherein the particle of interest is in focus; (c) locating the particle of interest in the specimen with reference to X and Y coordinates of the particle in the selected two-dimensional sectional representation and the Z-level of the selected two-dimensional sectional representation; and (d) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

DETAILED DESCRIPTION

Figure 1:
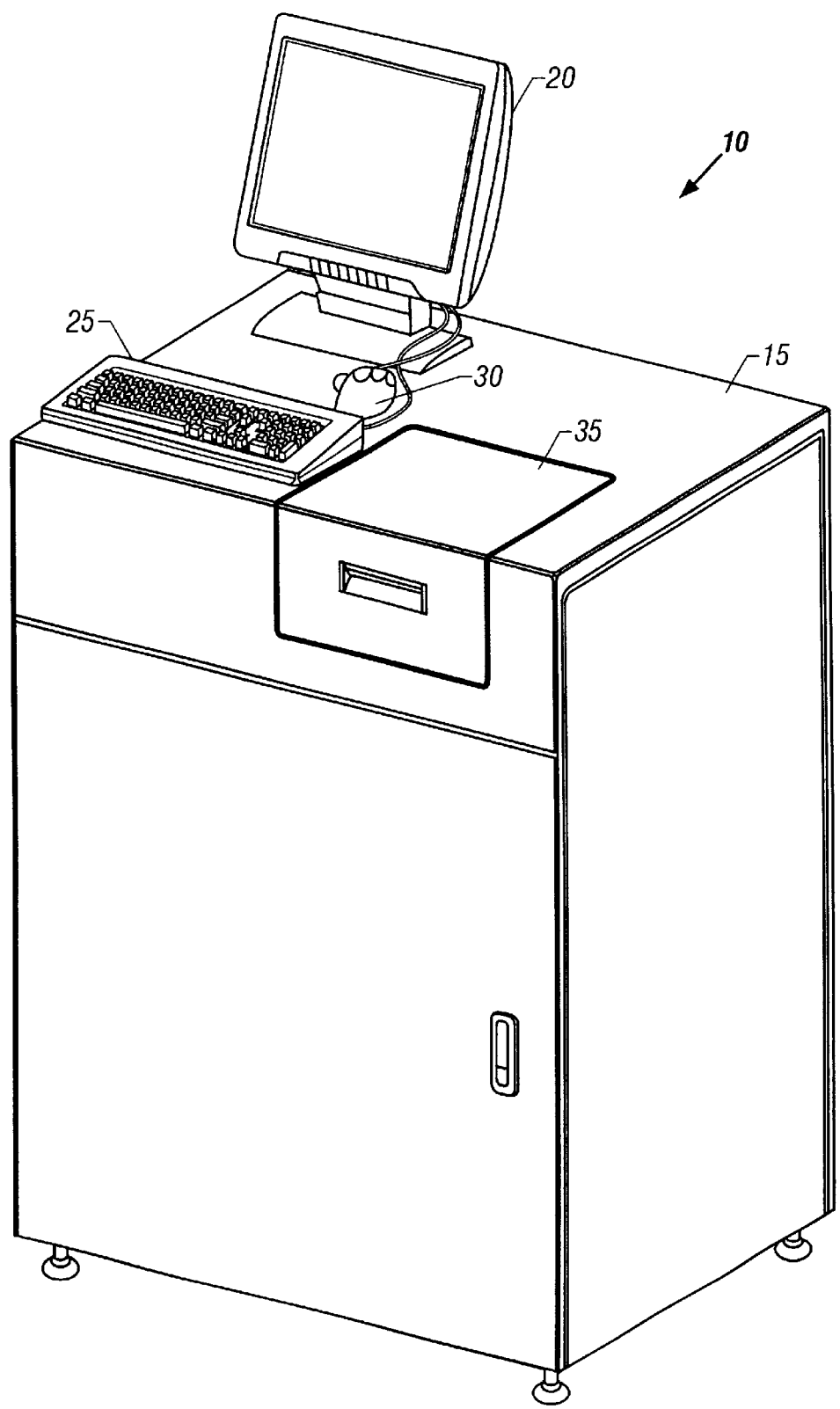
FIG. 1 is a perspective view of one embodiment of a cell treatment apparatus and illustrates the outer design of the housing and display.

This invention provides methods and apparatus for selectively targeting and electromagnetically irradiating specific particles in a specimen, for the purpose of inducing a response in the targeted particles. In one embodiment, the invention can be used to target a particular cell or subset of cells in a biological specimen. A cell can be targeted by microscopically imaging or otherwise detecting a distinguishing feature relative to other particles of the specimen. A cell once targeted can be irradiated with electromagnetic radiation to induce any of a variety of responses including necrosis, activation or inhibition of a stage in the cell cycle or development, change in gene expression or a change in cellular composition such as by uptake of an exogenous molecule or release of a caged or subcellular compartmentalized ion or molecule. An advantage of the apparatus and methods of the invention is that particular cells within a mixed population found in a typical biological specimen can be individually targeted and electromagnetically affected, without substantially affecting non-targeted cells within the specimen. Furthermore, the invention provides for automation of the apparatus or methods thereby allowing high-throughput processing of a specimen.

As used herein the term "electromagnetically affecting," when used in reference to a particle, is intended to mean changing at least one property of the particle by intersecting the particle with electromagnetic radiation energy. The term can include a property that is changed transiently such as electronic excitation state or permanently such as chemical composition or structure. When used in reference to a cell the changed property can include viability, membrane integrity, cell cycle stage, gene expression level, intracellular pH, intracellular composition, subcellular or cytosolic ion concentration or developmental stage and the like.

As used herein the term "discerning," when used in reference to a particle in a specimen, is intended to mean distinguishing the particle from at least one other component of the specimen according to a detectable property of the particle. The term can include distinguishing based on shape, size, optical properties, chemical composition, density, mass, presence or absence of a natural or synthetic label, affinity for a label or presence or absence of an associated chemical or biological activity.

As used herein the term "focal volume" is intended to mean a three-dimensional portion of an irradiated region in space, or in a specimen, that receives a higher amount of electromagnetic energy than received by any other portion of the region. The term can include a three-dimensional portion defined by a focal point to which rays of electromagnetic radiation converge or from which they appear to diverge after passing through an optical system, where the rays contacting the optical system can be collimated or non-collimated. The term can also include a portion defined by the intersection of two or more beams of electromagnetic radiation such that the portion receives higher energy than those regions through which each individual beam passes. The three-dimensional portion can define a portion of a specimen that receives an amount of electromagnetic radiation that substantially affects only the portion while an envelope of specimen surrounding the portion is substantially unaffected by the radiation.

As used herein, the term "specimen" is intended to mean any type of composition having particles within a three-dimensional environment. The term can include a biological specimen such as a tissue having cells or other particles. The specimen may be enclosed by, or associated with, a container. The container can be constructed to maintain the sterility and viability of the cells. Further, the specimen may incorporate, or be associated with, a cooling or heating apparatus to keep it above or below ambient temperature during operation of the apparatus or methods described herein. The specimen container, if one is used, can be made of a material that is compatible with the use of the illumination laser, back-light illuminator, and treatment laser, such that it transmits adequate energy without being substantially damaged itself.

A particle of the specimen can be a microscopic particle such as a cell, cell aggregate, virus, subcellular compartment such as an organelle, or large macromolecule such as a ribosome or chromosome. The "cells" used in the apparatus or method can be any biological cells, including procaryotic and eucaryotic cells, such as animal cells, plant cells, yeast cells, bacteria cells, human cells and non-human primate cells. The cells can be taken from organisms or harvested from cell cultures.

As used herein, the term "focal planar region" is intended to mean a viewed region in three-dimensional space that is elongated in two dimensions and substantially confined between two parallel planes that are orthogonal to the direction of view. The viewed region can be a slice or section of a specimen or portion of such a slice or section. Thus, a focal planar region of a specimen can be used to produce a sectional image of the specimen. The midplane of a focal planar region is intended to mean the plane that is parallel to and midway between the two parallel planes that confine the focal planar region.

The invention provides a method for electromagnetically affecting a particle of interest in a specimen. The method includes the steps of (a) obtaining a plurality of nonidentical two-dimensional sectional representations of the specimen in which the particle of interest is discernable in at least one of the sectional representations; (b) combining the plurality of sectional two-dimensional representations to produce a three-dimensional representation of the specimen; (c) locating the particle of interest in three dimensions based on the three-dimensional representation; and (d) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

The invention further provides a method for electromagnetically affecting a particle of interest in a specimen. The method includes the steps of (a) focusing a plurality of detectors on a plurality of focal planar regions in a specimen; (b) obtaining a plurality of two-dimensional sectional representations each corresponding to one of the focal planar regions, wherein a particle of interest can be discerned in at least one of the two-dimensional sectional representations; (c) storing the plurality of two-dimensional sectional representations in a computer memory; (d) combining the plurality of two-dimensional sectional representations to produce a three-dimensional representation of at least a portion of the specimen; (e) locating the particle of interest in the specimen based on the three-dimensional representation of at least a portion of the specimen; and (f) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

Further provided by the invention is a method for electromagnetically affecting a particle of interest in a specimen. The method includes the steps of: (a) obtaining a plurality of two-dimensional sectional representations of the specimen at different Z-levels, wherein the particle of interest is discernable in at least one of the sectional representations; (b) selecting a two-dimensional sectional representation from the plurality of two-dimensional sectional representations wherein the particle of interest is in focus; (c) locating the particle of interest in the specimen with reference to X and Y coordinates of the particle in the selected two-dimensional sectional representation and the Z-level of the selected two-dimensional sectional representation; and (d) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

The methods of the invention can be used to selectively identify, and individually target with an electromagnetic radiation beam, specific cells within a cell population for the purpose of electromagnetically affecting and thereby inducing a response in the targeted cells. The population of cells can be a mixed population in a biological specimen including a tissue such as from an organ or biological fluid such as blood. A specimen used in a method of the invention can also be homogenous in origin such as in a cell culture. A cell within a specimen that is targeted and electromagnetically affected can include a tumor cell, non-tumor cell, fibroblast, T-cell or teratoma-forming cell, to name a few.

The cells can be targeted according to a variety of properties that distinguish the cells from others in the specimen. A property useful in distinguishing a cell can be its morphological characteristics such as shape or size and physiological characteristics such as the location or the presence or absence of one or more detectable marker. For example, a label having specificity for a target cell can be used in a mixed population to distinguish the target cell. The cells targeted by the apparatus and methods herein are those that are selectively labeled, or otherwise distinguished from others in the specimen such that a focal volume produced by a treatment electromagnetic radiation source can be specifically directed to the targeted cells.

The chosen label can be any that substantially identifies and distinguishes the first population of cells from the second population of cells. The marker need not be destructive nor permanently associated with the cell. For example, monoclonal antibodies that are directly or indirectly tagged with a fluorochrome can be used as specific labels. Other examples of cell surface binding labels include non-antibody proteins, lectins, carbohydrates, or short peptides with selective cell binding capacity. Membrane intercalating dyes, such as PKH-2 and PKH-26, could also serve as a useful distinguishing label indicating mitotic history of a cell.

Many membrane-permeable reagents are also available to distinguish living cells from one another based upon selected criteria. For example, phalloidin indicates membrane integrity, tetramethyl rhodamine methyl ester (TMRM) indicates mitochondrial transmembrane potential, monochlorobimane indicates glutathione reductive stage, carboxymethyl fluorescein diacetate (CMFDA) indicates thiol activity, carboxyfluorescein diacetate indicates intracellular pH, fura-2 indicates intracellular $Ca^{2+}$ level, and 5,5',6,6'-tetrachloro-1,1',3,3'-tetraethylbenzimidazolo carbocyanine iodide (JC-1) indicates membrane potential. Cell viability can be assessed by the use of fluorescent SYTO 13 or YO PRO reagents. Similarly, a fluorescently-tagged genetic probe (DNA or RNA) could be used to label cells which carry a gene of interest, or express a gene of interest. Further, cell cycle status could be assessed through the use of Hoechst 33342 dye to label existing DNA combined with bromodeoxyuridine (BrdU) to label newly synthesized DNA.

To provide even greater flexibility in the ability to distinguish target cells from non-target cells, combinations of two or more labels, each with a different fluorochrome, can be used. For example, one antibody labeled with phycoerythrin (PE) and another antibody labeled with Texas Red® could be used to identify target cells that express one, both, or neither of the antigens recognized by the antibodies. A cell can also be identified according to a combination of present and absent labels compared to other cells in the specimen being processed. One skilled in the art could use a variety of multi-color labeling approaches to identify specific cell subpopulations within a complex mixture of cells.

A cell can also be targeted based on expression of an endogenous or exogenous reporter gene. Reporter genes useful for labeling a cell include the green fluorescent protein (GFP) and derivatives thereof, beta-galactosidase, and luciferase. Additionally, cells can be detected according to the presence or absence of a recombinantly fused reporter polypeptide such as a polyhistidine tag (Qiagen; Chatsworth, Calif.), antibody epitope such as the flag peptide (Sigma; St Louis, Mo.), glutathione-S-transferase (Amersham Pharmacia; Piscataway, N.J.), cellulose binding domain (Novagen; Madison, Wis.), calmodulin (Stratagene; San Diego, Calif.), staphylococcus protein A (Pharmacia; Uppsala, Sweden), maltose binding protein (New England BioLabs; Beverley, Mass.) or strep-tag (Genosys; Woodlands, Tex.). Reporter genes such as those described above can be constructed and detected using known methods as described in Sambrook et al., *Molecular Cloning: A Laboratory Manual,* 2nd ed., Cold Spring Harbor Press, Plainview, N.Y. (1989); Sambrook et al., *Molecular Cloning: A Laboratory Manual,* 3rd ed., Cold Spring Harbor Press, Plainview, N.Y. (2001); Ausubel et al. (*Current Protocols in Molecular Biology* (Supplement 47), John Wiley & Sons, New York (1999)).

It should be noted that if no specific label is available for cells of the first population, the method can be implemented in an inverse fashion by utilizing a specific label for cells of the non-target population. For example, in hematopoietic cell populations, the CD34 or ACC-133 cell markers can be used to label only the primitive hematopoietic cells, but not the other cells within the mixture. In this embodiment, cells of the first population are identified by the absence of the label, and are thereby targeted by the energy beam.

A specimen can be imaged and the three-dimensional coordinates of a target cell in the specimen determined as follows. Focal planar regions of the specimen occurring at different depths within the specimen can be observed and used to generate sectional images of the specimen. A particle can be identified and located in a selected in-focus sectional image as described in more detail below. Alternatively, a three dimensional image of the specimen can be reconstructed by arranging neighboring sectional images. A target cell can be identified in the three dimensional image according to an above-described distinguishing feature and its relative location in the specimen identified by a set of coordinates in three-dimensions. The coordinates of the target cell can then be used to aim a treatment electromagnetic radiation beam at the target cell.

After cells of the first population are identified, a treatment electromagnetic radiation beam, such as from a laser, collimated or focused non-laser light, RF energy, accelerated particle, focused ultrasonic energy, electron beam, or other radiation beam, is used to deliver a targeted dose of energy that induces the pre-determined response in at least one of the cells of the first population, without substantially affecting cells of the second population. The response can be lethal or non-lethal. Examples of responses that can be electromagnetically induced in the methods of the invention include changes in viability, membrane integrity, cell cycle stage, gene expression level, intracellular pH, intracellular composition, subcellular or cytosolic ion concentration or developmental stage and the like as will be described in further detail below.

Another response that can be electromagnetically induced is photobleaching. In photobleaching, a label in the form of a dye, such as rhodamine 123, GFP, fluorescein isothiocyanate (FITC), or phycoerythrin, is added to the specimen before the instant methods are commenced. After the population of cells has time to interact with the dye, the energy beam is used to bleach a region of individual cells in the population. Such photobleaching studies can be used to study the motility, replenishment, dynamics and the like of cellular components and processes.

Another response is internal molecular uncaging. In such a process, the specimen is combined with a caged molecule prior to the commencement of the instant methods. Such caged molecules include the β-2,6-dinitrobenzyl ester of L-aspartic acid or the 1-(2-nitrophenyl)ethyl ether of 8-hydroxypyrene-1,3,6-tris-sulfonic acid. Similarly, caging groups including alphacarboxyl-2-nitrobenzyl (CNB) and 5-carboxylmethoxy-2-nitrobenzyl (CMNB) can be linked to biologically active molecules as ethers, thioethers, esters, amines, or similar functional groups. The term "internal molecular uncaging" refers to the fact that the molecular uncaging takes place on the surface or within the cell. Such uncaging experiments study rapid molecular processes such as cell membrane permeability and cellular signaling.

Yet another response is external molecular uncaging. This uses approximately the same process as internal molecular caging. However, in external molecular uncaging, the uncaged molecule is not attached to or incorporated into the targeted cells. Instead, the responses of the surrounding targeted cells to the caged and uncaged variants of the molecule are imaged by the instant apparatus and methods.

As discussed above, multiple cell subpopulations can be identified with the appropriate use of specific labels and illumination sources. Further, multiple cellular responses can be induced with the appropriate use of treatment lasers and treatment substances added to the biological specimen. By extension, the simultaneous identification and processing of different cell subpopulations (i.e. to induce different responses) in parallel is possible. For example, one cell subpopulation can be identified and targeted for induction of necrosis, while another cell subpopulation in the same specimen can be targeted for optoporation. As the process is carried out, both cell subpopulations are treated in the appropriate manner, under control of the computer.

In addition to the use of colorometric dyes, embodiments of the invention also include a camera that images a plurality of colors. For example, in one embodiment, a color CCD camera is used to capture a color image of a population of cells. Because different cells are targeted by different colored compounds, images can be gathered that distinguish, on the basis of color, various cell types in a mixed population. For example, the identity of a cancer cell can be confirmed by its binding to two different colored compounds. A camera that detects these two colors is then able to confirm the identity of the cancer cell more reliably then if the system only relied on a single identifying compound.

The invention further provides an apparatus for electromagnetically affecting a particle of interest in a specimen. The apparatus includes (a) a stage capable of supporting the specimen; (b) a detector including at least one camera, wherein the detector is capable of resolving a particle of interest within the specimen; (c) a means for locating the particle of interest in three dimensions; (d) a means for focusing electromagnetic radiation to a focal volume within the specimen; and (e) a means for adjusting the relative positions of the stage and electromagnetic radiation focusing means, thereby positioning the particle of interest within the focal volume.

FIG. 1 is an illustration of one embodiment of a cell treatment apparatus 10. The cell treatment apparatus 10 includes a housing 15 that stores the inner components of the apparatus. The housing includes laser safety interlocks to ensure safety of the user, and also limits interference by external influences (e.g., ambient light, dust, etc.). Located on the upper portion of the housing 15 is a display unit 20 for displaying captured images of cell populations in a three-dimensional environment during treatment. These images are captured by a camera array, as will be discussed more specifically below. A keyboard 25 and mouse 30 are used to input data and control the apparatus. An access door 35 provides access to a movable stage that holds a specimen container of cells undergoing treatment.

Figure 2:
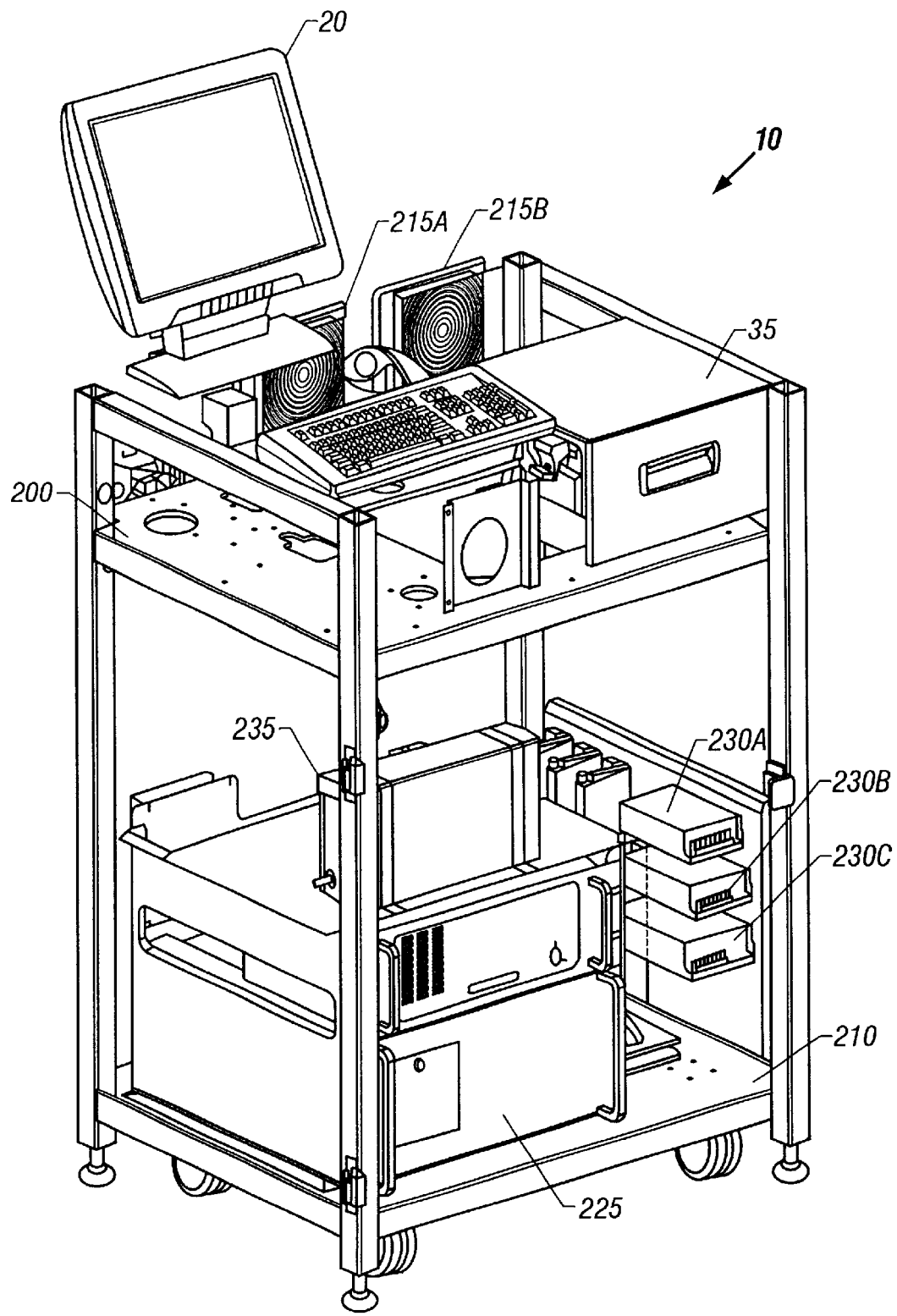
FIG. 2 is a perspective view of one embodiment of a cell treatment apparatus with the outer housing removed and the inner components illustrated.

An interior view of the apparatus 10 is provided in FIG. 2. As illustrated, the apparatus 10 provides an upper tray 200 and lower tray 210 that hold the interior components of the apparatus. The upper tray 200 includes a pair of intake filters 215A and B that filter ambient air being drawn into the interior of the apparatus 10. Below the access door 35 is the optical subassembly which is mounted to the upper tray 200 and is discussed in greater detail below with regard to FIGS. 3 through 10.

On the lower tray 210 is a computer 225 which stores the software programs, commands and instructions that run the apparatus 10. In addition, the computer 225 provides control signals to the treatment apparatus through electrical signal connections for steering the laser to the appropriate spot on the specimen in order to treat the cells.

As illustrated, a series of power supplies 230A,B and C provide power to the various electrical components within the apparatus 10. In addition, an uninterruptable power supply 235 can be incorporated to allow the apparatus to continue functioning through short external power interruptions.

Figure 3:
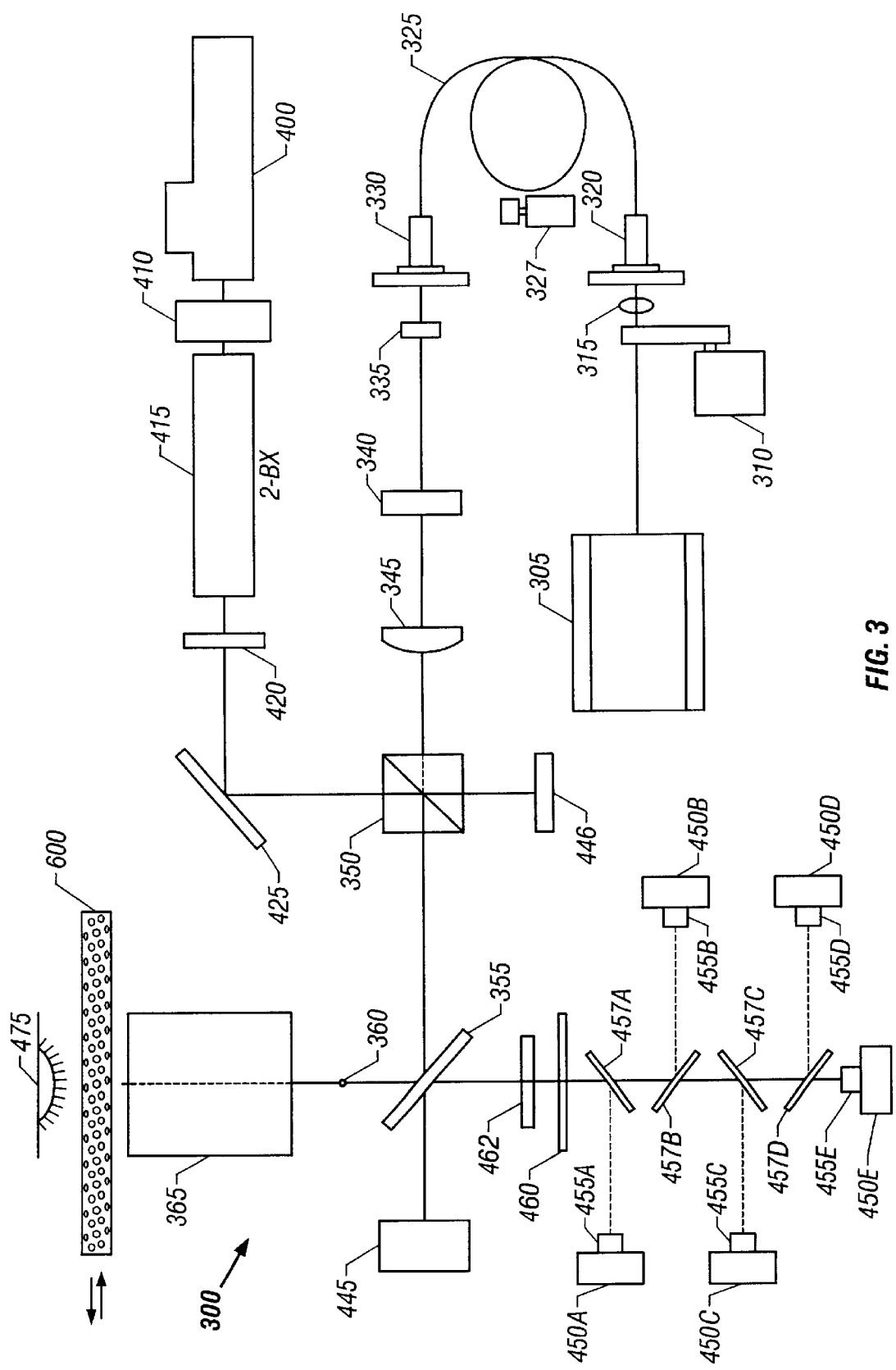
FIG. 3 is a block diagram of the optical subassembly design for one embodiment of a cell treatment apparatus.

FIG. 3 provides a layout of one embodiment of an optical subassembly design 300 for an embodiment of a cell treatment apparatus 10. As illustrated, an illumination laser 305 provides a directed laser output that is used to excite a particular label that is attached to targeted cells within the specimen. In this embodiment, the illumination laser emits light at a wavelength of 532 nm in order to optically excite specific labels. Of course lasers that illuminate light of other wave lengths could also be used within the system. Once the illumination laser has generated a light beam, the light passes into a shutter 310 which controls the pulse length of the laser light.

After the illumination laser light passes through the shutter 310, it enters a ball lens 315 where it is focused into an SMA fiber optic connector 320. After the illumination laser beam has entered the fiber optic connector 320, it is transmitted through a fiber optic cable 325 to an outlet 330. By passing the illumination beam through the fiber optic cable 325, the illumination laser 305 can be positioned anywhere within the treatment apparatus and thus is not limited to only being positioned within a direct light pathway to the optical components. In one embodiment, the fiber optic cable 325 is connected to a vibrating motor 327 for the purpose of mode scrambling and generating a more uniform illumination spot.

After the light passes through the outlet 330, it is directed into a series of condensing lenses in order to focus the beam to the proper diameter for illuminating one frame of cells. As used herein, one frame of cells is defined as the portion of the biological specimen that is captured within one image captured by a single camera. This is described more specifically below.

Accordingly, the illumination laser beam passes through a first condenser lens 335. In one embodiment, this first lens has a focal length of 4.6 mm. The light beam then passes through a second condenser lens 340 which, in one embodiment, provides a 100 mm focal length. Finally, the light beam passes into a third condenser lens 345, which provides a 200 mm focal length. While the present invention has been described using specific condenser lenses, it should be apparent that other similar lens configurations that focus the illumination laser beam to an advantageous diameter would function similarly. Thus, this invention is not limited to the specific implementation of any particular condenser lens system.

Once the illumination laser beam passes through the third condenser lens 345, it enters a cube beamsplitter 350 that transmits the 532 nm wavelength of light emanating from the illumination laser. Preferably, the cube beamsplitter 350 is a 25.4 mm square cube (Melles-Griot, Irvine, Calif.). However, other sizes are anticipated to function similarly. In addition, a number of plate beamsplitters or pellicle beamsplitters could be used in place of the cube beamsplitter 350 to suit other embodiments. Those skilled in the art will be able to use beamsplitters having a variety of different transmission wavelengths according to the particular labels used, and wavelengths of the illumination laser and transmission laser.

Once the illumination laser light has been transmitted through the cube beamsplitter 350, it reaches a long wave pass mirror 355 that reflects the 532 nm illumination laser light to a set of galvanometer mirrors 360 that steer the illumination laser light, under computer control, through a scanning lens (Special Optics, Wharton, N.J.) 365 to a specimen. The galvanometer mirrors are controlled so that the illumination laser light is directed at the proper portion of the three-dimensional cell population in the frame of cells to be imaged. The scanning lens described in this embodiment of the invention includes a refractive lens. It should be noted that the term "scanning lens" as used in the present invention includes, but is not limited to, a system of one or more refractive or reflective optical elements used alone or in combination. Further, the scanning lens may include a system of one or more diffractive elements used in combination with one or more refractive and/or reflective optical elements. One skilled in the art will know how to design a scanning lens system in order to illuminate the proper cell population.

The light from the illumination laser is of a wavelength that is useful for illuminating the specimen. In this embodiment, energy from a continuous wave 532 nm Nd:YAG frequency-doubled laser (B&W Tek, Newark, Del.) reflects off the long wave pass mirror (Custom Scientific, Phoenix, Ariz.) 355 and excites fluorescent labels in the specimen. In one embodiment, the fluorescent tag is phycoerythrin (PE). Alternatively, Alexa 532 (Molecular Probes, Eugene, Oreg.) can be used as a fluorescent tag in this embodiment of the invention. Phycoerythrin and Alexa 532 have emission spectra with peaks near 580 nm, so that the emitted fluorescent light from the specimen is transmitted via the long wave pass mirror into the camera array. The use of the filter in front of the camera array blocks light that is not within the wavelength range of interest, thereby reducing the amount of background light entering the camera array. Those skilled in the art will be able to select appropriate filters based on the excitation wavelength, excitation and emission spectra of the label used and the optical properties of the long pass filter 355.

The 532 nm illumination laser is further capable of exciting multiple fluorochromes that will emit energy at different wavelengths. For example, PE, Texas Red®, and CyChrome™ can all be efficiently excited by a 532 nm laser. However, they emit energy with spectra that peak at 576 nm, 620 nm, and 670 nm, respectively. This difference in transmitted wavelengths allows the signal from each fluorochrome to be distinguished from the others. In this case, the range of wavelengths transmitted by the filter 460 is expanded. In addition, the camera array is used to capture the emitted light, so that the different signals are distinguished by the computer. Alternatively, the emitted light can be directed to three monochromatic cameras, each having a filter for selective observation of one of the specific fluorochrome's emission wavelengths. Fluorochromes having a variety of differing excitation and emission spectra can be used with appropriate filters and illumination sources to allow detection and differentiation of multiple signals from a single specimen. Those skilled in the art will be able to select fluorochromes that can be differentiated by a particular set of optical components by comparison of the excitation and emission spectra for the fluorochromes with consideration for the known illumination and detection wavelengths for the optical components.

Yet another embodiment involves replacing the single fixed filter 460 with a movable filter cassette or wheel that provides different filters that are moved in and out of the optical pathway. In such an embodiment, fluorescent images of different wavelengths of light are captured at different times during cell processing. The images are then analyzed and correlated by the computer, providing multicolor information about each cell target or the cell population as a whole.

It is generally known that many other devices could be used in this manner to illuminate the specimen, including, but not limited to, a lamp such as an arc lamp or quartz halogen lamp. Examples of arc lamps useful in the invention include mercury arc lamps or xenon arc lamps. One skilled in the art will know that an appropriate lamp can be chosen based on a variety of factors including average radiance across the spectrum, radiance in specific regions of the spectrum, presence of spectral lines, radiance at spectral lines, or arc size. A light-emitting diode (LED) or laser other than the Nd:YAG frequency-doubled laser described above can also be used in the invention. Thus, the invention can include an ion laser such as argon ion or krypton ion laser, Helium neon laser, Helium cadmium laser, dye laser such as a rhodamine 6G laser, YAG laser or diode laser. One skilled in the art can choose an appropriate laser or lamp according to desired properties such as those described above or in Shapiro, *Practical flow cytometry*, 3$^{rd}$ Ed. Wiley-Liss, New York (1995).

Advantages of the Nd:YAG frequency-doubled laser described above include high intensity, relatively efficient use of energy, compact size, and low generation of heat. It is also generally known that other fluorochromes with different excitation and emission spectra could be used in such an apparatus with the appropriate selection of illumination source, filters, and long and/or short wave pass mirrors. For example, Texas Red®, allophycocyanin (APC), and PharRed™ could all be excited with a 633 nm HeNe illumination laser, whereas fluoroisothiocyanate (FITC), PE, and CyChrome™ could all be excited with a 488 nm Argon illumination laser. One skilled in the art could utilize many other optical layouts with various components in the invention in order to illuminate cells so that they return fluorescent energy in multiple wavelengths. The illumination sources described above can be used alone or in combination with other sources to provide a wide variety of illumination wavelengths within a single instrument, thereby allowing the use of many distinguishable labels simultaneously.

The invention can be configured to illuminate the specimen in any wavelength or wavelength range between 100 nanometers and 30 micrometers including ultra violet (UV) which occurs in the range of about 200 to 390 nm, visible (VIS) occurring in the range of about 390 to 770 nm, and infrared (IR) in the range of about 0.77 to 25 micrometers. A particular wavelength or wavelength range can be produced from a radiation source having a specified output range as described above. As also exemplified above, appropriate optical filters can be chosen to selectively pass, reflect or block radiation based on wavelength. Optical filters useful in the invention include interference filters in which multiple layers of dielectric materials pass or reflect radiation according to constructive or destructive interference between reflections from the various layers. Interference filters are also referred to in the art as dichroic filters, or dielectric filters. Also useful in the invention are absorptive filters which prevent passage of radiation having a selective wavelength or wavelength range by absorption. Absorptive filters include colored glass or liquid.

A filter used in the invention can have one or more particular filter transmission characteristics including, bandpass, short pass and long pass. A band pass filter selectively passes radiation in a wavelength range defined by a center wavelength of maximum radiation transmission ($T_{max}$) and a bandwidth and blocks passage of radiation outside of this range. $T_{max}$ defines the percentage of radiation transmitted at the center wavelength. The bandwidth is typically described as the full width at half maximum (FWHM) which is the range of wavelengths passed by the filter at a transmission value that is half of $T_{max}$. A band pass filter useful in the invention can have a FWHM of 10 nanometers (nm), 20 nm, 30 nm, 40 nm or 50 nm. A long pass filter selectively passes higher wavelength radiation as defined by a $T_{max}$ and a cut on wavelength. The cut on wavelength is the wavelength at which radiation transmission is half of $T_{max}$, and as wavelength increases above the cut on wavelength transmission percentage increases and as wavelength decreases below the cut on wavelength transmission percentage decreases. A short pass filter selectively passes lower wavelength radiation as defined by a $T_{max}$ and a cut off wavelength. The cut off wavelength is the wavelength at which radiation transmission is half of $T_{max}$, and as wavelength increases above the cut off wavelength transmission percentage decreases and as wavelength decreases below the cut off wavelength transmission percentage increases. A filter of the invention can have a $T_{max}$ of 50–100%, 60–90% or 70–80%.

In addition to the illumination laser 305, a treatment laser 400 is present to irradiate the targeted cells once they have been identified by the detector. In one embodiment, the radiation beam from the treatment laser induces necrosis of targeted cells within the cell population. As shown, the treatment laser 400 outputs an energy beam of 523 nm that passes through a shutter 410. Although in the embodiment described here the exemplary laser outputs an energy beam having a 523 nm wavelength, other electromagnetic radiation sources, such as those described above with respect to the illumination source, are also within the scope of the present invention and can be selected according to the particular response desired in the target particle.

Once the treatment laser energy beam passes through the shutter 410, it enters a beam expander (Special Optics, Wharton, N.J.) 415 which adjusts the diameter of the energy beam to an appropriate size at the plane of the specimen. Following the beam expander 415 is a half-wave plate 420 which controls the polarization of the beam. The treatment laser energy beam is then reflected off a fold mirror 425 and enters the cube beamsplitter 350. The treatment laser energy beam is reflected by 90° in the cube beamsplitter 350, such that it is aligned with the exit pathway of the illumination laser light beam. Thus, the treatment laser energy beam and the illumination laser light beam both exit the cube beamsplitter 350 along the same light path. From the cube beamsplitter 350, the treatment laser beam reflects off the long wave pass mirror 355, is steered by the galvanometers 360, thereafter enters the scanning lens 365 which focuses the treatment electromagnetic radiation beam to a focal volume within the three-dimensional specimen. The focal volume receives a sufficient amount of electromagnetic radiation energy to kill a cell within the focal volume. However, cells in the envelope surrounding the focal volume are not substantially affected by the radiation from the treatment laser. Thus, cells in the envelope surrounding the focal volume are not killed by the treatment laser. However, a focal volume need not entirely encompass a particle of interest such that a particle of interest having at least a portion within the focal volume can be substantially electromagnetically affected in the methods and apparatus of the invention.

It should be noted that a small fraction of the illumination laser light beam passes through the long wave pass mirror 355 and enters a power meter sensor (Gentec, Palo Alto, Calif.) 445. The fraction of the beam entering the power sensor 445 is used to calculate the level of power emanating from the illumination laser 305. In an analogous fashion, a small fraction of the treatment laser energy beam passes through the cube beamsplitter 350 and enters a second power meter sensor (Gentec, Palo Alto, Calif.) 446. The fraction of the beam entering the power sensor 446 is used to calculate the level of power emanating from the treatment laser 400. The power meter sensors are electrically linked to the computer system so that instructions/commands within the computer system capture the power measurement and determine the amount of energy that was emitted from the treatment laser. Thus, the system provides feedback control for altering the power of each laser to suit a particular application.

The energy beam from the treatment laser is of a wavelength that is useful for achieving a response in the cells. In the presently described embodiment, the radiation source produces a focal volume having sufficient energy to kill a cell. More specifically, a pulsed 523 nm Nd:YLF frequency-doubled laser is used to heat a localized volume of fluid containing the targeted cell, such that it is induced to die. The rate and efficiency of cell death is dependent upon the actual temperature achieved in the cell, as described by Niemz, *Laser-tissue interactions: Fundamentals and applications*, Springer-Verlag, Berlin 1996. Briefly, induction of necrosis occurs at about 60° C. or higher due to denaturation and coagulation of proteins. Further heating to about 80° C. or higher causes a drastic increase in cell membrane permeability, further damaging the cell. The temperature required for reliable necrosis induction changes with exposure duration, rising about 3.5° C. for each 10-fold decrease in exposure duration. For example, necrosis can be induced following an exposure at about 72° C. for about 1 msec, whereas exposure at about 94° C. will induce necrosis after an exposure time of about 1 nsec. Thus, the treatment electromagnetic radiation beam wavelength and power can be selected to kill a cell within a few milliseconds, seconds or even minutes.

A Nd:YLF frequency-doubled, solid-state laser (Spectra-Physics, Mountain View, Calif.) is used because of its stability, high repetition rate of firing, and long time of maintenance-free service. However, most cell culture fluids and cells are relatively transparent to light in this green wavelength, and therefore relatively high fluences of energy are used to achieve cell death. A reduced amount of energy can be used for inducing cell death in methods where a dye is added to or present in the cell culture such that energy from the treatment laser is efficiently absorbed thereby heating the specimen. Specificity can also be achieved by selectively labeling target particles in a specimen, such as cells, with a dye and irradiating the specimen with a low fluence of radiation sufficient to affect the labeled particle but too weak to substantially affect non-labeled particles. In the example shown, the non-toxic dye FD&C red #40 (allura red) is used to absorb the 523 nm energy from the treatment laser. However, one skilled in the art could identify other laser/dye combinations that would result in efficient absorption of energy by the specimen. For example, a 633 nm HeNe laser's energy would be efficiently absorbed by FD&C green #3 (fast green FCF). Alternatively, a 488 nm Argon laser's energy would be efficiently absorbed by FD&C yellow #5 (sunset yellow FCF), and a 1064 run Nd:YAG laser's energy would be efficiently absorbed by Filtron (Gentex, Zeeland, Mich.) infrared absorbing dye. Through the use of an energy absorbing dye, the amount of energy required to kill a targeted within a cell population can be reduced since more of the treatment laser energy is absorbed in the presence of such a dye.

Another method of killing cells is to adjust the wavelength of radiation emitted from the treatment laser. The wavelength of the radiation emitted from the treatment laser can be any of a variety of wavelengths or wavelength ranges including those described above with respect to the illumination laser. Those skilled in the art will be able to use a variety of available lasers as a treatment laser in the apparatus of the invention such as those described above with respect to the illumination laser. For example, killing can be achieved by the use of an ultraviolet laser. Energy from a 355 nm Nd:YAG frequency-tripled laser will be absorbed by nucleic acids and proteins within the cell, resulting in cell death. In another embodiment, killing of cells can be achieved with the use of a near-infrared laser. Energy from a 2100 nm Ho:YAG laser or a 2940 run Er:YAG laser will be absorbed by water within the cell, resulting in cell death. Other electromagnetic radiation sources can be used alone or in combination with optical filters such as those described above to generate a treatment electromagnetic radiation beam for electromagnetically affecting a particle or cell in a focal volume.

Although this embodiment describes the killing of cells by the energy beam, one skilled in the art would recognize that other responses can also be induced in the cells by an energy beam, including photomechanical disruption, photodissociation, photoablation, and photochemical reactions, as reviewed by Niemz, supra. For example, a sufficient amount of energy can be supplied to the focal volume to specifically activate a photosensitive substance photodynamic therapy agent such as a hematoporphyrin derivative, tin-etiopurpurin or lutetium texaphyrin as described in Oleinick and Evans, The photobiology of photodynamic therapy: Cellular targets and mechanisms, *Rad. Res.* 150: S146–S156 (1998). Additionally, a small, transient pore could be made in the cell membrane (Palumbo et al., Targeted gene transfer in eukaryotic cells by dye-assisted laser optoporation, *J. Photochem. Photobiol.* 36:41–46 (1996)) to allow the entry of genetic or other material. This cell permeabilization response can be achieved through at least two potential mechanisms. The first is optoporation, using a laser directed toward cells and the surrounding media to induce shock waves, thereby causing small holes to form temporarily in the surface of nearby cells, allowing materials to non-specifically enter cells in the area. The second is optoinjection, using a laser directed at specific cells to selectively form a pore in the membranes of those cells targeted. Further, specific molecules in or on the cell, such as proteins or genetic material, could be inactivated by the directed energy beam (Grate and Wilson, Laser-mediated, site-specific inactivation of RNA transcripts, *PNAS* 96:6131–6136 (1999); Jay, D. G., Selective destruction of protein function by chromophore-assisted laser inactivation, *PNAS* 85:5454–5458 (1988)). Also, photobleaching can be utilized to measure intracellular movements such as the diffusion of proteins in membranes and the movements of microtubules during mitosis (Ladha et al., *J. Cell Sci.*, 110(9):1041 (1997); Centonze and Borisy, *J. Cell Sci.* 100 (part 1):205 (1991); White and Stelzer, *Trends Cell Biol.* 9(2):61–5 (1999); Meyvis, et al., *Pharm. Res.* 16(8) :1153–62 (1999). Further, photolysis or uncaging, including multiphoton uncaging, of caged compounds can be utilized to control the release, with temporal and spatial resolution, of biologically active products or other products of interest (Theriot and Mitchison, *J. Cell Biol.* 119:367 (1992); Denk, *PNAS* 91(14):6629 (1994)). These mechanisms of inducing a response in a targeted cell via the use of electromagnetic radiation directed at specific targeted cells are also intended to be incorporated into the present invention.

An apparatus of the invention can include one or more treatment electromagnetic radiation beam as described above. For example, a plurality of electromagnetic radiation beams can originate from one or more electromagnetic radiation source such as a lamp or laser that is divided and redirected in a plurality of paths. The paths can end in a sigle focal volume or a plurality of focal volumes. Each path can pass through different optical components to produce treatment electromagnetic radiation beams of differing wavelength or intensity if desired. Alternatively or additionally, a plurality of treatment lasers can be used in an apparatus of the invention.

More than one laser can be directed to a specimen such that the electromagnetic radiation beams intersect at a focal volume within the specimen. The focal volume at which the electromagnetic radiation beams intersect will experience a higher intensity of radiation than other regions within the envelope surrounding the focal volume. The intensity and number of electromagnetic radiation beams intersecting the specimen can be selected to produce sufficient combined energy to electromagnetically affect a particle within the focal volume while individually producing an amount of energy that is not capable of substantially electromagnetically affecting particles outside of the focal volume. Two or more treatment electromagnetic radiation beams that intersect a focal volume of a specimen can have differing wavelengths and can irradiate a focal volume simultaneously or sequentially as desired to induce a particular electromagnetic effect or combination of electromagnetic effects. The wavelengths and intensities of the electromagnetic radiation beams can be selected from within the ranges described previously.

In addition to the illumination laser 305 and treatment laser 400, the apparatus includes a detector having an array of cameras 450A, 450B, 450C and 450D that capture images, or frames of the cell populations at stepped Z-levels (Z-levels are also referred to herein as depths of field). The camera array contains a plurality of cameras having views offset vertically with respect to each other which allows the array to capture cell images at various Z-levels, or depths, within the specimen. As illustrated in FIG. 3, each camera 450A, 450B, 450C, 450D and 450E is focused through a lens 455A, 455B, 455C, 455D and 455E, respectively to capture light reflected by a beamsplitter 457A, 457B, 457C and 457D, respectively. Prior to reaching the beamsplitters 457A, 457B, 457C and 457D the light from the specimen passes through a filter 460 to allow accurate imaging of the cells at the desired wavelengths without capturing stray background light occurring at other wavelengths. A stop 462 is positioned between the filter 460 and mirror 355 in order to prevent unwanted light from entering the camera array from angles not associated with the image from the specimen. The filter 460 is chosen to selectively pass light within a certain wavelength range. The wavelength range of transmitted light includes wavelengths emitted from the targeted cells upon excitation by the illumination laser 305, as well as those from a back-light source 475. The filter 460 selectively prevents passage of light in the wavelength region of the illumination laser which would otherwise saturate the detector or render the fluorescence signal undetectable.

The back-light source 475 is located above the specimen 600 to provide back-illumination of the specimen at a wavelength different from that provided by the illumination laser 305. In the embodiment described here, the back light source is an LED that emits light at 590 nm, such that it can be transmitted through the long wave pass mirror to be directed into the camera array. This back-illumination is useful for imaging cells whether or not there are fluorescent targets within the frame being imaged. The back-light can be used in attaining proper focus of the system, even when there are only unstained, non-fluorescent cells in the frame. In one embodiment, the back-light is mounted on the underside of the access door 35 (FIG. 2). Thus, the apparatus can be configured with an appropriate back light, illumination laser and optical filters to selectively pass illumination of a desired wavelength to the camera array. Other wavelengths of light are prevented from passing through the filter 460, and being recorded by the camera array 450.

It should be noted that in the presently described embodiment, the detector includes a camera array having a plurality of charge-coupled devices (CCD). The cameras can be placed to view different focal planar regions, each of the viewed focal planar regions being a different sectional image of the specimen. The detector can transmit the sectional images back to the computer system for processing. As will be described below, the computer system determines the coordinates of the targeted cells in the specimen by reference to one or more sectional images captured by the CCD camera array.

Figure 4:
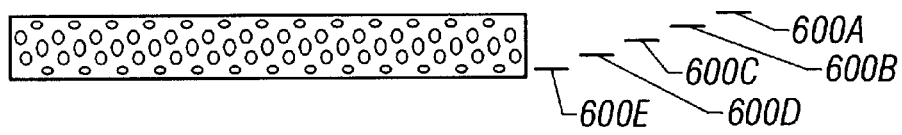
FIG. 4 is a front view of the relative focal planar regions achieved at stepped Z-levels by the CCD array.
Figure 5:
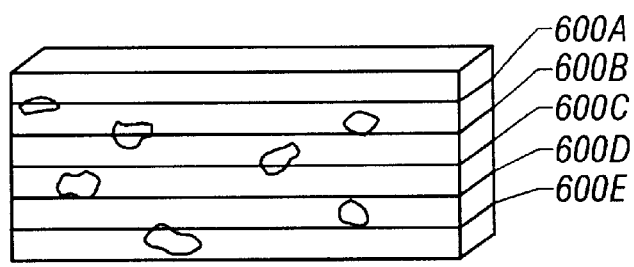
FIG. 5 is a perspective view of a specimen showing how the three-dimensional image processor module assembles the images captured by the CCD array at stepped Z-levels.
Figure 6:
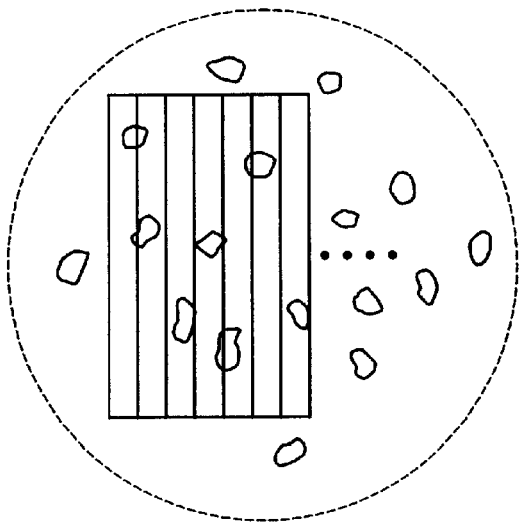
FIG. 6 is a bottom view of a specimen of cells illustrating the quadrants as seen by the CCD array. Each rectangular quadrant represents an image captured by a single camera focused at its respective Z-level.
Figure 7:
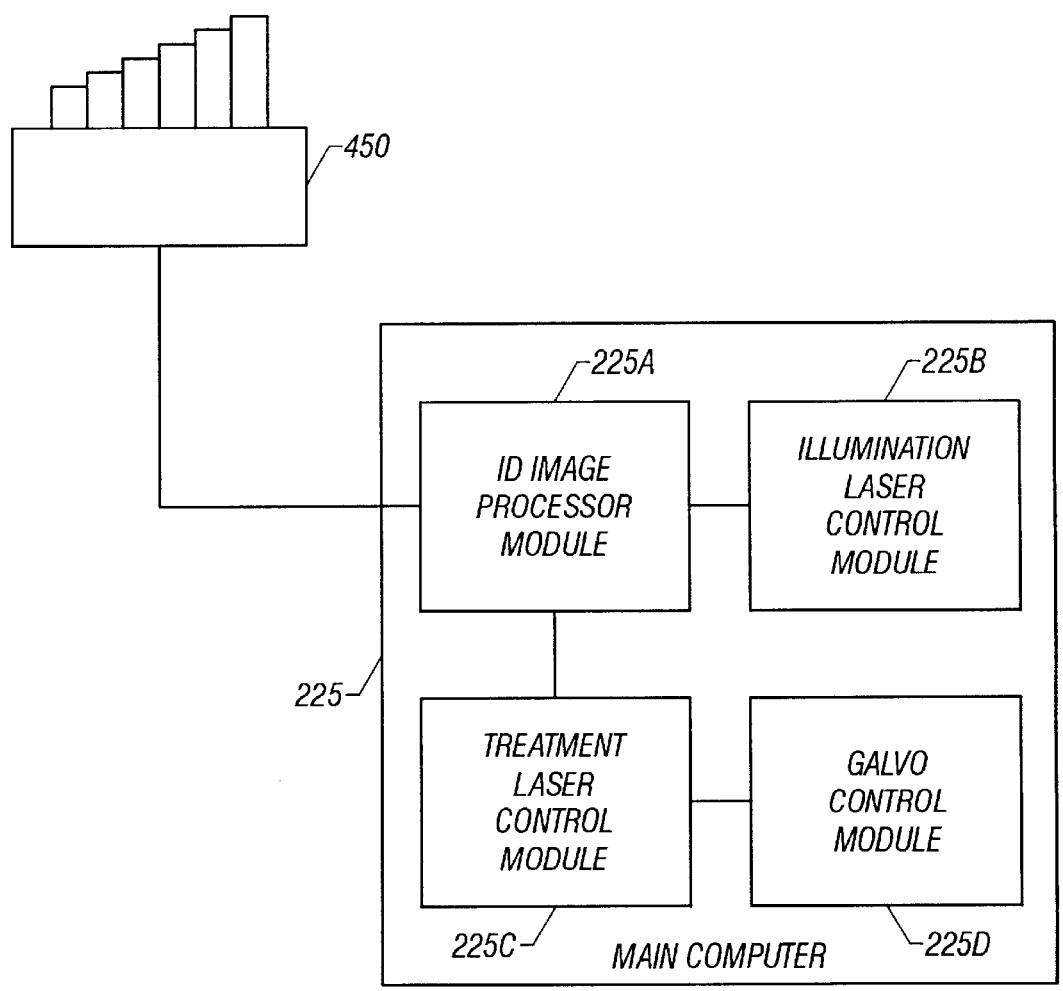
FIG. 7 is a block diagram of the optical subassembly that illustrates the interrelation of the CCD array with the cell treatment apparatus.

Referring generally to FIGS. 4 through 6, the use of the CCD camera array is illustrated. As illustrated, the views of the CCD cameras are substantially parallel and each CCD camera views a different focal length. Different focal planes can be viewed by the cameras by vertically offsetting each camera within the array or by placing focusing optics between the camera and specimen. Using such an arrangement it becomes possible to capture focused images of cells within focal planar regions observed at different depths of field within the specimen. As illustrated in FIG. 5, the focal planar regions observed at each depth of field, as indicated by sections 600A through 600E, can be captured as sectional images and then assembled by a three-dimensional image processor 225A of FIG. 7 to produce a three-dimensional volume image of the specimen. This image is then used to determine three coordinates for aiming the treatment laser to the appropriate location within the volume of the specimen.

The apparatus can produce sectional images at a variety of depths of field according to the configuration of optical devices. Those skilled in the art will be able to configure the detector to image at a shallow depth of field which includes a depth of less than 100 microns. Depending upon the size of the specimen the depth of field can be selected from 1, 2, 3, 4, 5, 6, 7, 8, 9, 10, 11, 12, 15, 20, 25, 30, 35, 40, 45, 50, 60, 70, 80 90 or 100 microns. For larger specimens even greater depths of field can be employed for deeper imaging.

The apparatus of the invention can be configured to capture images of the specimen at different resolutions or magnifications. This can be achieved by altering the property of the lens 455 in front of one or more cameras. A turret, cassette or wheel containing different lenses can be placed between the camera and specimen such that the magnification or resolution can be rapidly changed. The turret, cassette or wheel can be functionally attached to a positioning device for manual or automated changes in resolution or magnification during the course of or between specimen processing procedures.

A detector used in the apparatus can also include two or more cameras capable of imaging the specimen from different directions of view. Imaging from different directions of view, also referred to as stereo-imaging, can be used to reconstruct an image of the specimen. Two or more cameras can stereo-image a specimen when their different directions of view are separated by an angle selected from 1 to 180 degrees. The invention can include cameras having different directions of view separated by less than 1 degree, 2 degrees, 5 degrees, 10 degrees, 15 degrees, 20 degrees, 25 degrees, 30 degrees, 35 degrees, 40 degrees, 45 degrees, 50 degrees, 90 degrees or 180 degrees, wherein a degree is intended to be used consistent with mathematical usage wherein it is an angle subtending 1/360 of the circumference of a circle.

A detector used in the invention can include one or more cameras viewing a relatively shallow focal planar region, wherein the focal planar region can be refocused on different sections of the specimen. A particular camera view can be refocused to observe a specimen at different depths of field thereby obtaining different sectional images of the specimen. Such refocusing can be achieved by moving the camera. Other lower inertia components of the detector are preferably moved in order to achieve refocus and include lenses or mirrors placed in between the optical path of the camera and specimen. The component to be adjusted can be operably attached to a positioning device for manual or automated refocusing. Automated focusing can be achieved by incorporation of an automated positioning device that is capable of communicating with imaging processing devices such as those described below.

Any detector capable of converting radiation directed from a specimen or particle therein into a signal that can be subsequently manipulated or stored to determine the presence or quantity of a particle in a specimen can be used in the apparatus or methods of the invention. A detector can include a photodiode, photomultiplier tube or charge-coupled device. A detector can also include an imaging device that converts radiation directed from a specimen or particle therein to a set of signals that can be converted into a 3-dimensional representation of a specimen. Such an imaging device can include a camera such as a CCD camera, digital camera, film camera or photographic camera and the like. One skilled in the art will be able to choose a detector based on a variety of well known factors including, for example, compatibility with the radiation source used, sensitivity, spectral range of detection and compatibility with data processing devices.

Figure 8:
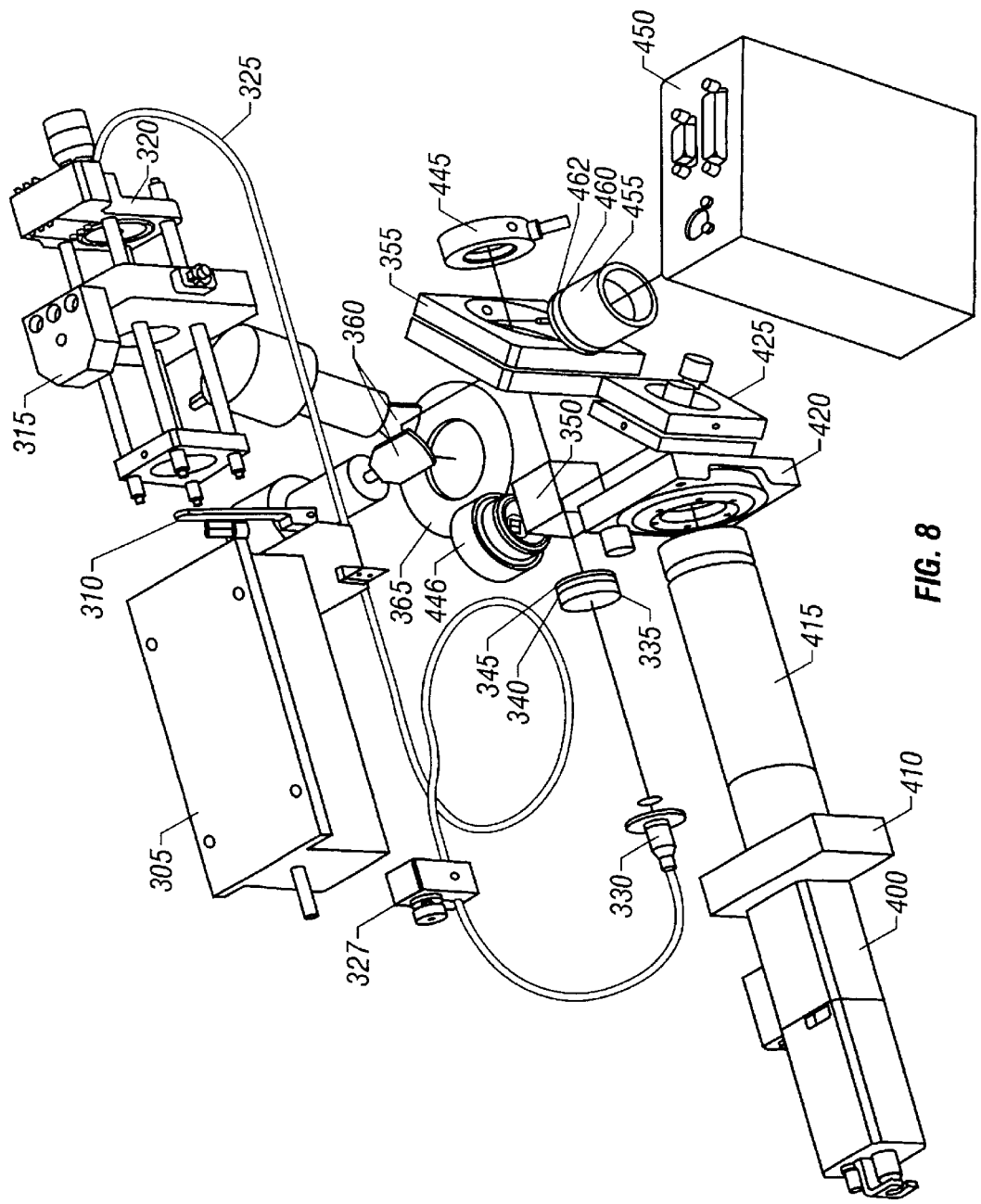
FIG. 8 is a perspective view of one embodiment of an optical subassembly within one embodiment of a cell treatment apparatus.

Referring now to FIG. 8, a perspective view of an embodiment of an optical subassembly is illustrated. As illustrated, the illumination laser 305 sends a light beam through the shutter 310 and ball lens 315 to the SMA fiber optic connector 320. The light passes through the fiber optic cable 325 and through the output 330 into the condenser lenses 335, 340 and 345. The light then enters the cube beamsplitter 350 and is transmitted to the long wave pass mirror 355. From the long wave pass mirror 355, the light beam enters the computer-controlled galvanometers 360 and is then steered to the proper frame of cells in the specimen through the scanning lens 365.

As also illustrated in the perspective drawing of FIG. 8, the treatment laser 400 transmits energy through the shutter 410 and into the beam expander 415. Energy from the treatment laser 400 passes through the beam expander 415 and passes through the half-wave plate 420 before hitting the fold mirror 425 and subsequently entering the cube beamsplitter 350 where it is reflected 90° to the long wave pass mirror 355, from which it is reflected into the computer controlled galvanometer mirrors 360. The galvanometer mirrors 360 can be adjusted to steer the treatment laser beam through the scanning lens 365 such that the beam strikes the portion of a specimen where a particular target cell is located. Accordingly, a desired response can be selectively induced in the target cell using the apparatus of the invention.

Figure 11:
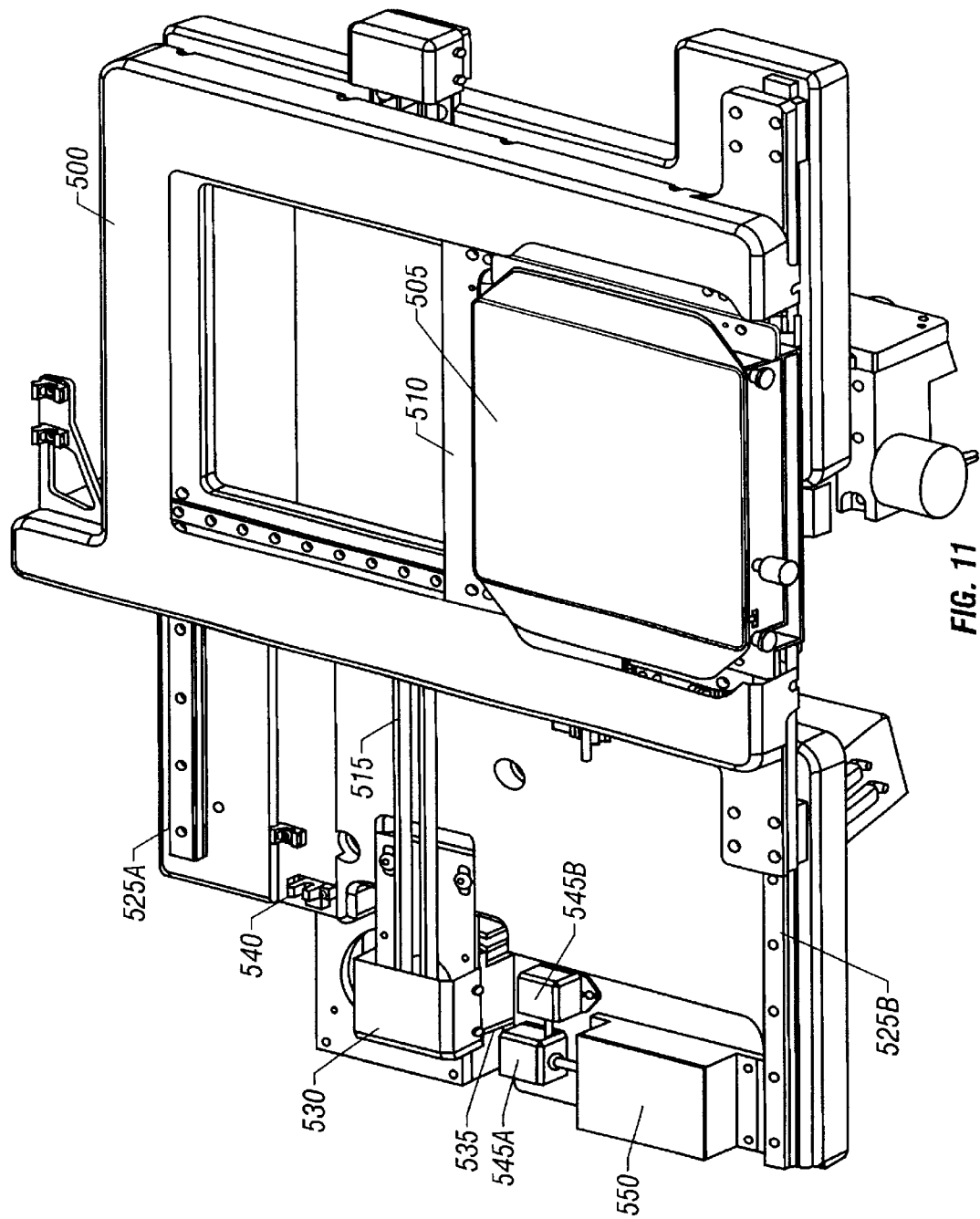
FIG. 11 is a top perspective view of the movable stage of the cell treatment apparatus.

In order to accommodate a very large surface area of specimen to treat, the apparatus includes a movable stage that mechanically moves the specimen container with respect to the scanning lens. Thus, once a specific subpopulation of cells within the scanning lens field-of-view has been treated, the movable stage brings another subpopulation of cells within the scanning lens field-of-view. As illustrated in FIG. 11, a computer-controlled movable stage 500 holds a specimen container 505 which contains a specimen 600 to be processed. The movable stage 500 is moved by computer-controlled servo motors along two axes so that the specimen container can be moved relative to the optical components of the instrument. The stage movement along a defined path is coordinated with other operations of the apparatus. In addition, specific coordinates can be saved and recalled to allow, return of the movable stage to positions of interest. Encoders on the x and y movement provide closed-loop feedback control of stage position.

A flat-field (F-theta) scanning lens 365 can be mounted below the movable stage. The scanning lens field-of-view comprises the portion of the specimen that is presently positioned above the scanning lens by the movable stage 500. The lens 365 can be mounted to a stepper motor that allows the lens 365 to be automatically raised and lowered (along the z-axis) for the purpose of focusing the system.

Figure 9:
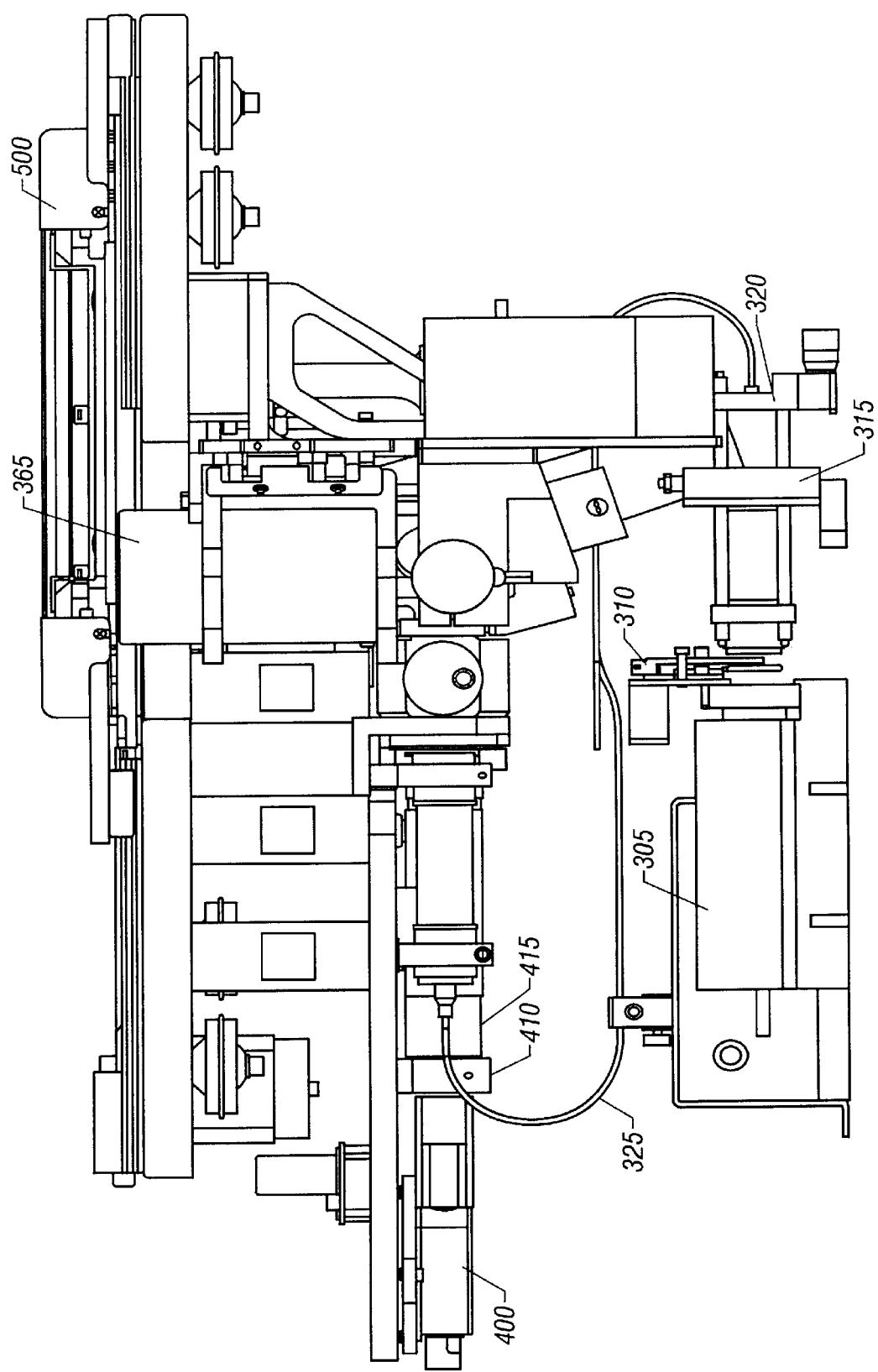
FIG. 9 is a side view of one embodiment of an optical subassembly that illustrates the arrangement of the scanning lens and the movable stage.
Figure 10:
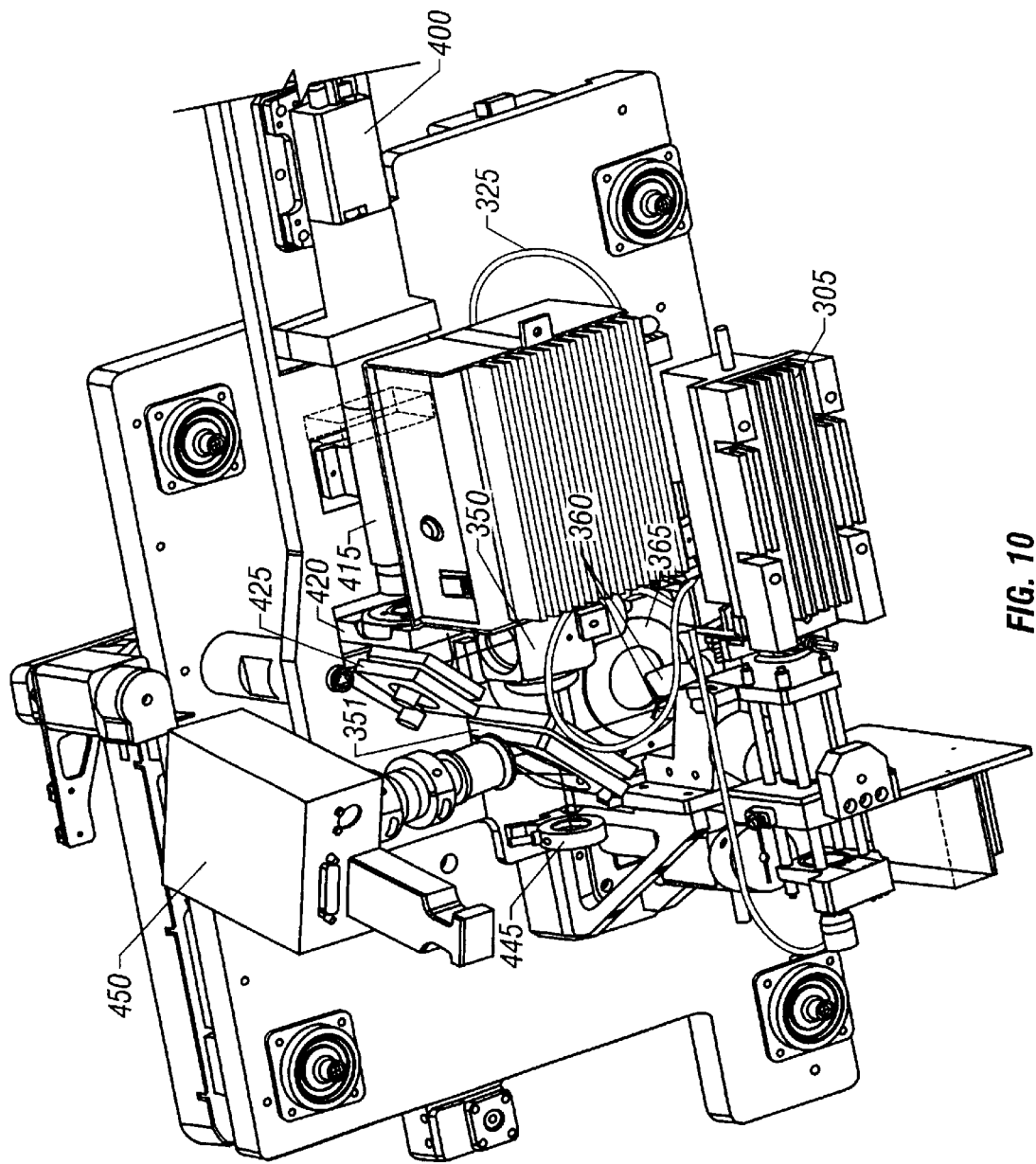
FIG. 10 is a bottom perspective view of one embodiment of an optical subassembly.

As illustrated in FIGS. 8–10, below the scanning lens 365 are the galvanometer-controlled steering mirrors 360 that deflect electromagnetic energy along two perpendicular axes. Behind the steering mirrors is the long wave pass mirror 355 that reflects electromagnetic energy of a wavelength shorter than 545 nm. Wavelengths longer than 545 nm are passed through the long wave pass mirror, directed through the filter 460, coupling lens 455, and into the CCD camera array, thereby producing an image of the appropriate size on the CCD sensor of the camera array 450 (See FIGS. 3 and 4). The magnification defined by the combination of the scanning lens 365 and coupling lens 455 can be chosen to reliably detect single cells while maximizing the area viewed in one frame by each camera. Although a CCD camera array (DVC, Austin, Tex.) is illustrated in this embodiment, the camera can be any type of detector or image gathering equipment known to those skilled in the art, as described above. The optical subassembly of the apparatus is preferably mounted on a vibration-damping platform to provide stability during operation as illustrated in FIGS. 2 and 9.

Referring now to FIG. 11, a top view of the movable stage 500 is illustrated. As shown, a specimen container can be detachably mounted in the movable stage 500. The specimen container 505 rests on an upper axis nest plate 510 that is designed to move in the forward and backward direction with respect to the movable stage 500. A stepper motor can be connected to the upper axis nest plate 510 and computer system so that commands from the computer direct forward or backward movement of the specimen container 505.

The movable stage 500 is also connected to a timing belt 515 that provides side-to-side movement of the movable stage 500 along a pair of bearing tracks 525A and B. The timing belt 515 attaches to a pulley housed under a pulley cover 530. The pulley is connected to a stepper motor 535 that drives the timing belt 515 to result in side-to-side movement of the movable stage 500. The stepper motor 535 is electrically connected to the computer system so that commands within the computer system control side-to-side movement of the movable stage 500. A travel limit sensor 540 connects to the computer system and causes an alert if the movable stage travels beyond a predetermined lateral distance.

A pair of accelerometers 545A and B is preferably incorporated on this platform to register any excessive bumps or vibrations that may interfere with the apparatus operation. In addition, a two-axis inclinometer 550 is preferably incorporated on the movable stage to ensure that the specimen container is level, thereby reducing the possibility of gravity-induced motion in the specimen container.

The specimen chamber has a fan with ductwork to eliminate condensation on the specimen container, and a thermocouple to determine whether the specimen chamber is within an acceptable temperature range. Additional fans are provided to expel the heat generated by the electronic components, and appropriate filters are used on the air intakes 215A and B (see FIG. 2).

The computer system 225 controls the operation and synchronization of the various components of electronic hardware described above. The computer system can be any commercially available computer that can interface with the hardware. One example of such a computer system is an Intel Pentium® IV-based computer running the Microsoft Windows® 2000 operating system. Software is used to communicate with the various devices, and control the operation in the manner that is described below.

When the apparatus is first initialized, the computer loads files from the hard drive into RAM for proper initialization of the apparatus. A number of built-in tests are automatically performed to ensure the apparatus is operating properly, and calibration routines are executed to calibrate the cell treatment apparatus. Upon successful completion of these routines, the user is prompted to enter information via the keyboard and mouse regarding the procedure that is to be performed (e.g. patient name, ID number, etc.). Once the required information is entered, the user is prompted to open the access door 35 and load a specimen onto the movable stage.

Once a specimen is in place on the movable stage and the door is closed, the computer passes a signal to the stage to move into a home position. The fan is initialized to begin warming and defogging of the specimen. During this time, cells within the specimen are allowed to settle to the bottom surface. In addition, during this time, the apparatus may run commands that ensure that the specimen is properly loaded, and is within the focal range of the system optics. For example, specific markings on the specimen container can be located and focused on by the system to ensure that the scanning lens has been properly focused on the bottom of the specimen container. After a suitable time, the computer turns off the fan to prevent excess vibrations during treatment, and cell treatment processing begins.

First, the computer instructs the movable stage to be positioned over the scanning lens so that the first area of the specimen to be treated is directly in the scanning lens field-of-view. The galvanometer mirrors are instructed to move such that the center frame within the field-of-view is imaged in the camera. As discussed below, the field imaged by the scanning lens is separated into a plurality of frames. Each frame is the proper size so that the cells within the frame are effectively imaged by the camera array.

The back-light 475 is then activated in order to illuminate the field-of-view so that it can be brought into focus by the scanning lens. Once the scanning lens has been properly focused upon the specimen, the computer system divides the field-of-view into a plurality of frames so that each frame is analyzed separately by the camera array. This methodology allows the apparatus to process a plurality of frames within a large field-of-view without moving the mechanical stage. Because the galvanometers can move from one frame to the next very rapidly compared to the mechanical steps involved in moving the stage, this method results in an extremely fast and efficient apparatus.

The apparatus of the invention can further include an image processing device 225A for combining one or more two-dimensional representations of a specimen and producing a three-dimensional representation. A two-dimensional or three-dimensional representation refers to an image or any characterization of a specimen, or portion thereof, that specifies the coordinates of at least one particle of interest therein such as a graphical or tabular list of coordinates or a set of computer commands that can be used to produce an image.

Initially, one or more two-dimensional representations such as two-dimensional sectional images can be captured by the camera array and stored to a memory in the computer. Although, a single two-dimensional image can contains sufficient information to produce a three dimensional representation of a specimen, it may be desirable to process two or more or a plurality of two-dimensional images to produce a three-dimensional image. Instructions in the computer can produce or calculate a three dimensional representation such as a three-dimensional image. A three-dimensional image calculated as such can be analyzed with respect to the size, shape, number, or other object features in the image at each stepped Z-level. If necessary, the computer instructs the z-axis motor attached to the scanning lens to raise or lower in order to improve focus on the frame of interest. The galvanometer-controlled mirrors are then instructed to image a first frame, within the field-of-view, in the camera array. Once the galvanometer mirrors are pointed to the first frame in the field-of-view, the shutter in front of the illumination laser is opened to illuminate the first frame through the galvanometer mirrors and scanning lens. The camera array captures an image of any fluorescent emission from the specimen in the first frame of cells. Once the image has been acquired, the shutter in front of the illumination laser is closed and a software program (Epic, Buffalo Grove, Ill.) within the computer processes the image.

The image processing device 225A can include the capability of virtual autofocusing by searching sectional images of a specimen and identifying a sectional image that is in-focus. Virtual autofocusing does not require production of a three-dimensional representation of any part of the specimen and can, therefore, be performed prior to or absent formation of a three-dimensional representation. A plurality of sectional representations such as sectional images can be obtained as described above using one or more cameras viewing different focal planar regions. Virtual autofocusing can be achieved by analyzing multiple sectional images and selecting an in-focus image. Subsequent image processing can then be selectively carried out for the in-focus sectional image in order to efficiently identify a desired target particle. Thus, a particle of interest can be identified or located in a specimen based on its X and Y coordinates in the in-focus sectional image and the Z-level of the sectional image. The X and Y coordinates as used herein refer to coordinates in two dimensions forming a plane orthogonal to the direction of view. A plurality of in-focus sectional images selected by virtual autofocusing can be used to calculate a three-dimensional image as described above.

Although real-time autofocusing can be used in the invention, virtual autofocusing provides the advantage of more rapid throughput. Specifically, real-time autofocusing often requires multiple adjustments of optical components and re-imaging until an in-focus sectional image is obtained. In contrast, when a plurality of fixed cameras are placed to view non-overlapping focal planar regions, at least one camera will have a focused view without the need to move any component of the detector. Subsequently, the images can be analyzed using algorithms similar to those used in real-time autofocusing methods without the requirement for time-consuming movement of optical components and reacquisition of images.

Known autofocusing algorithms such as those used in microscopy or autofocus cameras can be used to analyze sectional images and identify an in-focus sectional image in the apparatus and methods of the invention. An example of an autofocus method that can be used in the apparatus or methods of the invention is binary search autofocus. Binary search autofocus can be performed virtually by preselecting two sectional images between which an in-focus sectional image is thought to exist and iteratively reducing the number of intervening sectional images until one having a desired focus is identified. The iterations include the steps of selecting a sectional image that is halfway between the boundary sectional images, evaluating the selected sectional image for a predetermined focus value and further reducing the boundary distance until a sectional image having the desired focus value is identified. Alternatively, a sequential autofocus method can be used in which sectional images are analyzed in a stepwise fashion starting from a preselected initial sectional image.

In another embodiment, the detector can capture an image of a two-dimensional specimen. Virtual autofocusing will work if the depth of the specimen is less than the depth of field of the detector view. Virtual autofocusing can be carried out as described above to identify or locate the X and Y coordinates for a particle of interest located in the two-dimensional specimen. The particle identified as such can be targeted and electromagnetically affected using an apparatus or method of the invention.

The power sensor 445, discussed above, detects the level of light intensity emitted by the illumination laser. Based on the measured intensity, the computer can determine if an appropriate amount of light has illuminated the frame of cells for the particular application. In the event a particular threshold has not been obtained or the signal surpasses a desired maximum the laser intensity can be adjusted and another illumination and image capture sequence performed. Such iteration can be carried out until the appropriate conditions are achieved or after a preselected number of iterations the system can pause or indicate in an error condition that is communicated to the operator.

The threshold or maximum energy levels will depend upon the particular application of the apparatus or methods of the invention. The term "threshold" refers to the amount of energy sufficient to change a particular property. For example, a threshold amount of electromagnetic energy can be an amount sufficient to kill a cell, to transiently permeabilize a membrane or cell, to induce a cell cycle stage, to activate or repress gene expression, to increase or decrease intracellular pH within a defined range, or to alter a morphological, metabolic or developmental stage of a cell. Other cells in the same specimen that do not receive radiation at or beyond the threshold will not undergo the particular change. A range of electromagnetic energy used in the apparatus or methods of the invention can be defined by a threshold and a ceiling. A "ceiling" is intended to mean an amount of energy that is greater than a threshold amount and sufficient to induce an unwanted change in a particular property. The ceiling can be defined by any detectable change including those described above in relation to a threshold energy. Thus, a range of electromagnetic energy used in the invention can include an amount of energy sufficient to transiently permeabilize a membrane or cell without causing permanent permeabilization or cell death.

Shuttering of illumination light can be used to reduce undesirable heating and photobleaching of the specimen and to provide a fluorescent signal in a desired range of detection. An image analysis algorithm is run to locate the x-y-z centroid coordinates of all targeted cells in the frame by reference to features in the captured image. If there are targets in the image, the computer calculates the three-dimensional coordinates of the target locations in relation to the movable stage position and field-of-view, and then positions the galvanometer-controlled mirrors to point the treatment electromagnetic radiation beam to the location of the first target in the first frame of cells. It should be noted that the z-coordinate may be calculated by the algorithm based in part upon the focal length of the camera that captured the image. It should further be noted that only a single frame of cells within the field-of-view has been captured and analyzed at this point. Thus, there should be a relatively small number of identified targets within this sub-population of the specimen. Moreover, because the camera array is pointed to a smaller population of cells, a higher magnification is used so that each target is imaged by many pixels within the CCD camera.

Once the computer system has positioned the galvanometer controlled mirrors to point to the location of the first targeted cell within the first frame of cells, the treatment laser is fired for a brief interval so that the first targeted cell is given an appropriate dose of energy. The power sensor 446 discussed above detects the level of energy that was emitted by the treatment laser, thereby allowing the computer to calculate if it was within a desired range to induce a response in the targeted cell. The power of the treatment laser can be adjusted and the treatment laser fired at the same target again. The iterative targeting, firing, and sensing steps can be repeated until appropriate conditions are achieved or up to a predetermined number of rounds after which the iteration is paused or an error message communicated to the operator. In another embodiment, the treatment laser can be fired once at more than one, a group or all of the target cells within a frame, and subsequently the computer can direct the target laser to return to any cells that did not receive a sufficient level of energy to induce a response.

Once all of the targets have been irradiated with the treatment laser in the first frame of cells, the mirrors can be positioned to the second frame of cells in the field-of-view, and the processing repeated at the point of frame illumination and camera imaging. This processing can be continued for all frames within the field-of-view above the scanning lens. When all of these frames have been processed, the computer instructs the movable stage to move to the next field-of-view in the specimen, and the process repeated from the back-light illumination and auto-focus steps. Frames and fields-of-view can be overlapped to reduce the possibility of inadvertently missing areas of the specimen. Once the specimen has been fully processed, the operator is signaled to remove the specimen, and the apparatus is immediately ready for the next specimen. Although the text above describes the analysis of fluorescent images for locating targets, those skilled in the art will understand that the non-fluorescent back-light LED illumination images can be useful for locating target cells based on other properties such as those viewable in a standard microscope based on absorbance, transmittance or refraction of light.

The galvanometer mirrors provide the advantage of controlling the imaging of successive frames and the irradiation of successive targets. One brand of galvanometer is the Cambridge Technology, Inc. model number 6860 (Cambridge, Mass.). This galvanometer can reposition very accurately within a fraction of a millisecond, making the processing of large areas and many targets possible within a reasonable amount of time. In addition, the movable stage can be used to move specified areas of the specimen into the scanning lens field-of-view. This combination of movements can be automated providing increased throughput of the apparatus or methods.

It should be understood that other embodiments of the invention are also possible. For example, a movable stage, similar to a conveyer belt, could be included to continuously move a specimen of cells through the above-described process. Error signals continuously generated by the galvanometer control boards are monitored by the computer to ensure that the mirrors are in position and stable before an image is captured, or before a target is fired upon, in a closed-loop fashion.

In one embodiment, the apparatus described herein is capable of electromagnetically affecting particles in at least 1, 2, 3, 4, 5, 6, 7, 8, 9, or 10 square centimeters of a biological specimen per minute. In another embodiment, the apparatus described herein processes at least 0.25, 0.5, 1, 2, 3 or 4 million cells of a biological specimen per minute. The rate at which the apparatus operates can be measured as the number of particle containing focal volumes that are electromagnetically affected per minute. The apparatus can electromagnetically affect at least 1, 2, 3, 4, 5, 6, 8, 10, 15, 20, 30, 60, 100, 300, 500, 1000, 3000, 5000, 10000, 30000, 50000, 100000, 300000, or 500000 separate focal volumes in the specimen per minute. Furthermore, the rate of imaging can be at the rate of at least 1 Hz, 2 Hz, 3 Hz, 4 Hz, 5 Hz, 6 Hz, 8 Hz, 10 Hz, 15 Hz, 30 Hz, 50 Hz, 100 Hz, 150 Hz, 300 Hz, 500 Hz, or 1000 Hz.

One embodiment allows in vitro maintenance of the biological specimen in the apparatus, such that it can be monitored and processed periodically in situ. This is accomplished by maintaining the specimen under a standard tissue culture environment of 37° C. In this manner, specific cells in the specimen are followed over time, periodically assessing their state, and/or periodically rendering treatment to those specific cells. The system includes software and computer memory storage for providing the apparatus with the ability to record cell locations and thereafter direct the movable stage to return to those recorded locations such that large specimens can be repeatedly processed in a scanning mode.

Of course, many variations of the above-described embodiments are possible, including alternative methods for illuminating, imaging, and targeting the cells. For example, movement of the specimen relative to the scanning lens could be achieved by keeping the specimen substantially stationary while the scanning lens is moved. Steering of the illumination beam, images, and energy beam could be achieved through any controllable reflective or diffractive device, including prisms, piezo-electric tilt platforms, or acousto-optic deflectors. Additionally, the apparatus can image/process from either below or above the specimen. Because the apparatus is focused through a movable scanning lens, the illumination and energy beams are directed to different focal planes along the z-axis. Thus, portions of the specimen that are located at different vertical heights are specifically imaged and processed by the apparatus in a three-dimensional manner. The sequence of the steps could also be altered without changing the process. For example, one might locate and store the coordinates of all targets in the specimen, and then return to the targets to irradiate them with energy one or more times over a period of time.

To optimally process the specimen, it should be placed on a substantially flat surface so that a large portion of the specimen appears within a narrow range of focus. The density of cells on this surface can, in principle, be at any value. However, increasing the cell density can minimize the total surface area required to be scanned or detected in the apparatus or methods of the invention.

The following examples illustrate the use of the described method and apparatus in different applications.

EXAMPLE 1

Autologous HSC Transplantation

A patient with a B cell-derived metastatic tumor in need of an autologous HSC transplant is identified by a physician. As a first step in the treatment, the patient undergoes a standard HSC harvest procedure, resulting in collection of approximately $1 \times 10^{10}$ hematopoietic cells with an unknown number of contaminating tumor cells. The harvested cells are enriched for HSC by a commercial immunoaffinity column (Isolex® 300, Nexell Therapeutics, Irvine, Calif.) that selects for cells bearing the CD34 surface antigen, resulting in a population of approximately $3 \times 10^8$ hematopoietic cells, with an unknown number of tumor cells. The mixed population is thereafter contacted with anti-B cell antibodies (directed against CD20 and CD23) that are conjugated to phycoerythrin, and anti-CD34 antibodies that are conjugated to CyChrome™.

The mixed cell population is then placed in a sterile specimen container on a substantially flat surface near confluence, at approximately 500,000 cells per square centimeter. The specimen is placed on the movable stage of the apparatus described above, and all detectable tumor cells are identified by the presence of the phycoerythrin tag and absence of the CyChrome™ tag, and are then targeted with a lethal dose of energy from a treatment laser. The design of the apparatus allows the processing of a clinical-scale transplant specimen in under 4 hours. The cells are recovered from the specimen container, washed, and then cryopreserved. Before the cells are reinfused, the patient is given high-dose chemotherapy to destroy the tumor cells in the patient's body. Following this treatment, the processed cells are thawed at 37° C. and are given to the patient intravenously. The patient subsequently recovers with no remission of the original cancer.

EXAMPLE 2

Allogeneic HSC Transplantation

In another embodiment, the significant risk and severity of graft-versus-host disease in the allogeneic HSC transplant setting can be combated. A patient is selected for an allogeneic transplant once a suitable donor is found. Cells are harvested from the selected donor as described in the above example. In this case, the cell mixture is contacted with phycoerythrin-labeled anti-CD3 T-cell antibodies. Alternatively, specific allo-reactive T-cell subsets could be labeled using an activated T-cell marker (e.g. CD69) in the presence of allo-antigen. The cell population is processed by the apparatus described herein, thereby precisely defining and controlling the number of T-cells given to the patient. This type of control is advantageous, because administration of too many T-cells increases the risk of graft-versus-host disease, whereas too few T-cells increases the risk of graft failure and the risk of losing of the known beneficial graft-versus-leukemia effect. The present invention and methods are capable of precisely controlling the number of T-cells in an allogeneic transplant.

EXAMPLE 3

Tissue Engineering

In another application, the present apparatus is used to remove contaminating cells in inocula for tissue engineering applications. Cell contamination problems exist in the establishment of primary cell cultures required for implementation of tissue engineering applications, as described by Langer and Vacanti, Sci. Amer. 280:86–89 (1999). In particular, chondrocyte therapies for cartilage defects are hampered by impurities in the cell populations derived from cartilage biopsies. Accordingly, the present invention is used to specifically remove these types of cells from the inocula. For example, a cartilage biopsy is taken from a patient in need of cartilage replacement. The specimen is then grown under conventional conditions as described in Brittberg et al., N.E.J. Med. 331:889–895 (1994). The culture is then stained with a specific label for any contaminating cells, such as fast-growing fibroblasts. The cell mixture is then placed within the apparatus described and the labeled, contaminating cells are targeted by the treatment laser, thereby allowing the slower growing chondrocytes to fully develop in culture.

EXAMPLE 4

Stem Cell Therapy

Yet another embodiment involves the use of embryonic stem cells to treat a wide variety of diseases. Since embryonic stem cells are undifferentiated, they can be used to generate many types of tissue that would find use in transplantation, such as cardiomyocytes and neurons. However, undifferentiated embryonic stem cells that are implanted can also lead to a jumble of cell types which form a type of tumor known as a teratoma as described in Pedersen, Sci. Amer. 280:68–73 (1999). Therefore, therapeutic use of tissues derived from embryonic stem cells must include rigorous purification of cells to ensure that only sufficiently differentiated cells are implanted. The apparatus described herein is used to eliminate undifferentiated stem cells prior to implantation of embryonic stem cell-derived tissue in the patient.

EXAMPLE 5

Generation of Human Tumor Cell Cultures

In another embodiment, a tumor biopsy is removed from a cancer patient for the purpose of initiating a culture of human tumor cells. However, the in vitro establishment of primary human tumor cell cultures from many tumor types is complicated by the presence of contaminating primary cell populations that have superior in vitro growth characteristics over tumor cells, and the limited number of tumor cells obtainable from such a specimen. For example, contaminating fibroblasts represent a major challenge in establishing many cancer cell cultures. The disclosed apparatus is used to particularly label and destroy the contaminating cells, while leaving the biopsied tumor cells intact. Accordingly, the more aggressive primary cells will not overtake and destroy the cancer cell line. The apparatus described within allows purification of cells with relatively high yield, which is particularly important in application where the starting cell number is limited. The high yield of purified cells from the disclosed apparatus provides a significant advantage over other cell purification methods.

EXAMPLE 6

Generation of a Specific mRNA Expression Library

The specific expression pattern of genes within different cell populations is of great interest to many researchers, and many studies have been performed to isolate and create libraries of expressed genes for different cell types. For example, knowing which genes are expressed in tumor cells versus normal cells is of great potential value as described in Cossman et al., Blood 94:411–416 (1999). Due to the amplification methods used to generate such libraries (e.g. PCR), even a small number of contaminating cells can result in an inaccurate expression library. One approach to overcome this problem is the use of laser capture microdissection (LCM), in which a single cell is used to provide the starting genetic material for amplification as described in Schutze et al., Nat. Biotech. 16:737–742 (1998). Accurate purification of a significant cell number prior to extraction of mRNA would enable the generation of a highly accurate expression library, one that is representative of the cell population being studied, without biases due to single cell expression or expression by contaminating cells. The methods and apparatus described in this invention can be used to purify cell populations with high yield so that no contaminating cells are present during an RNA extraction procedure.

Within a human prostate tumor, there are multiple cell types, each of which lead to metastatic disease. To understand the basis of prostate cancer and its progression, the tools of genomics such as DNA sequencing of normal prostate and cancer prostate cDNAs (expressed sequence tags, or ESTs) and DNA array comparison of normal and cancerous tissues have been used to investigate the distinct patterns of gene expression in normal prostate and in different prostate tumors. It has been shown that different prostate cell subpopulations with different surface antigens have different mRNA expression profiles. Using the apparatus disclosed herein, primary human prostate tumors are purified for specific cell subpopulations to investigate their gene expression. For example, four populations of primary prostate cells are purified for mRNA analysis by binding antibodies against specific cell markers to new cell surfaces. The purified populations are: CD44'CD13' normal basal, CD44'CD13' basal cell-like cancer, CD57'CD13' normal luminal, and CD57'CD13 luminal cell-like cancer epithelial cells. Understanding the nature of each subpopulation, and its relation to disease onset and progression, could lead to new diagnostic and therapeutic approaches in the treatment of the disease.

EXAMPLE 7

Transfection, Monitoring, and Purification of a Specific Cell Population

Many research and clinical gene therapy applications are hampered by the inability to transfect an adequate number of a desired cell type without transfecting other cells that are present. The method of the present invention would allow selective targeting of cells to be transfected within a mixture of cells. By generating a photomechanical shock wave at or near a cell membrane with a targeted energy source, a transient pore can be formed, through which genetic or other material can enter the cell. This method of gene transfer has been called optoporation. The apparatus described above can selectively induce optoporation in the cells of interest in a rapid, automated, targeted manner.

For example, bone marrow cells are plated in a specimen container having a solution containing plasmid DNA to be transfected. The plasmid DNA encodes a therapeutic gene (e.g. MDR), as well as a marker gene (e.g. green fluorescent protein). PE-labeled antibodies (anti-CD34) having specificity for stem cells are added into the medium and bind to the stem cells. The specimen container is placed within the cell processing apparatus and a first treatment laser is targeted to any cells that become fluorescent under the illumination laser light, thereby facilitating transfection of DNA specifically into the targeted cells. The cells are maintained in situ at 37° C., all targeted cells being periodically analyzed for expression of green fluorescent protein to indicate successful transfection with the plasmid DNA. After 48 hours, all cells not expressing green fluorescent protein are eliminated with a second treatment laser, thereby yielding a pure population of stem cells expressing the transfected genes.

EXAMPLE 8

Selection of Desirable Clones in a Biotechnology Application

In many biotechnology processes where cell lines are used to generate a valuable product, it is desirable to derive clones that are very efficient in producing the product. This selection of clones is often carried out manually, by inspecting a large number of clones that have been isolated in some manner. The present invention would allow rapid, automated inspection and selection of desirable clones for production of a particular product. For example, hybridoma cells that are producing the greatest amounts of antibody can be identified by a fluorescent label directed against the Fc region. Cells with no or dim fluorescent labeling are targeted by the treatment laser for killing, leaving behind the best producing clones for use in antibody production.

EXAMPLE 9

Automated Monitoring of Cellular Responses

Automated monitoring of cellular responses to specific stimuli is of great interest in high-throughput drug screening. Often, a cell population in one well of a well-plate is exposed to a stimulus, and a fluorescent signal is then captured over time from the cell population as a whole. Using the methods and apparatus described herein, more detailed monitoring could be done at the single cell level. For example, a cell population can be labeled to identify a characteristic of a subpopulation of cells that are of interest. This label is then excited by the illumination laser to identify those cells. Thereafter, the treatment laser is targeted at the individual cells identified by the first label, for the purpose of exciting a second label, thereby providing information about each cell's response. Since the cells are substantially stationary on a surface, each cell could be evaluated or treated multiple times, thereby providing temporal information about the kinetics of each cell's response. Also, through the use of the large area scanning lens and galvanometer mirrors, a relatively large number of wells could be quickly monitored over a short period of time.

As a specific example, consider the case of alloreactive T-cells as presented in Example 2 above. In the presence of allo-antigen, activated donor T-cells could be identified by CD69. Instead of using the treatment laser to target and kill these cells, the treatment laser could be used to examine the intracellular pH of every activated T-cell through the excitation and emitted fluorescence of carboxyfluorescein diacetate. The targeted laser allows the examination of only cells that are activated, whereas most screening methods evaluate the response of an entire cell population. If a series of such wells are being monitored in parallel, various agents could be added to individual wells, and the specific activated T-cell response to each agent could be monitored over time. Such an apparatus would provide a high-throughput screening method for agents that ameliorate the alloreactive T-cell response in graft-versus-host disease Based on this example, one skilled in the art could imagine many other examples in which a cellular response to a stimulus is monitored on an individual cell basis, focusing only on cells of interest identified by the first label.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. An apparatus for electromagnetically affecting a particle of interest in a specimen, comprising
   (a) a stage capable of supporting the specimen;
   (b) a detector comprising at least one camera,
      wherein the detector is capable of resolving a particle of interest within the specimen;
   (c) a means for locating the particle of interest in three dimensions;
   (d) a means for focusing electromagnetic radiation to a focal volume within the specimen; and
   (e) a means for adjusting the relative positions of the stage and electromagnetic radiation focusing means, thereby positioning the particle of interest within the focal volume, wherein the apparatus is capable of electromagnetically affecting particles in at least 10 separate focal volumes in the specimen per minute.

2. The apparatus of claim 1, wherein the detector is capable of obtaining a plurality of non-identical two-dimensional images, wherein a particle of interest is discernable in at least one of the two-dimensional images.

3. The apparatus of claim 1, wherein the apparatus is capable of electromagnetically affecting particles in at least 500,000 separate focal volumes in the specimen per minute.

4. The apparatus of claim 1, wherein the detector comprises a plurality of cameras capable of imaging the specimen from different directions of view.

5. The apparatus of claim 4, wherein the different directions of view are separated by an angle less than 45 degrees.

6. The apparatus of claim 1, wherein the detector comprises a charge-coupled device camera.

7. The apparatus of claim 1, wherein the means for locating the particle comprises a device for processing more than one two-dimensional representations to produce a three-dimensional representation.

8. The apparatus of claim 1, wherein the means for locating the particle comprises a computer memory capable of storing location coordinates for at least one particle of interest.

9. The apparatus of claim 1, wherein the adjusting means comprises an automated positioning device functionally connected to the electromagnetic radiation focusing means.

10. The apparatus of claim 9, wherein the means for locating the particle is capable of communicating with the automated positioning device.

11. The apparatus of claim 1, wherein the adjusting means comprises an automated positioning device functionally connected to the stage.

12. The apparatus of claim 11, wherein the means for locating the particle is capable of communicating with the automated positioning device.

13. The apparatus of claim 1, wherein the adjusting means comprises an automated positioning device functionally connected to the electromagnetic radiation focusing means and stage.

14. The apparatus of claim 13, wherein the means for locating the particle is capable of communicating with the automated positioning devices.

15. The apparatus of claim 1, further comprising an electromagnetic radiation source directed to the electromagnetic radiation focusing means.

16. The apparatus of claim 15, wherein the electromagnetic radiation source is at least one laser.

17. The apparatus of claim 16, wherein the radiation is convergent.

18. The apparatus of claim 15, wherein the at least one laser emits a wavelength between 100 nanometers and 30 micrometers.

19. The apparatus of claim 15, wherein the source comprises a plurality of lasers.

20. The apparatus of claim 19, wherein the radiation beams from the lasers intersect in the focal volume.

21. The apparatus of claim 19, wherein the lasers emit radiation of differing wavelengths.

22. The apparatus of claim 15, whereby the focal volume can comprise sufficient energy to kill a cell.

23. The apparatus of claim 15, whereby the focal volume can comprise sufficient energy to optoinject a cell.

24. The apparatus of claim 15, whereby the focal volume can comprise sufficient energy to inactivate a cell component.

25. The apparatus of claim 15, whereby the focal volume can comprise sufficient energy to activate a photosensitive agent.

26. The apparatus of claim 25, wherein the photosensitive agent is a caged compound, photodynamic therapy agent or fluorophore.

27. The apparatus of claim 1, further comprising an illuminating device placed to illuminate the specimen.

28. The apparatus of claim 27, wherein the illuminating device comprises a lamp.

29. The apparatus of claim 27, wherein the illuminating device comprises a laser.

30. The apparatus of claim 27, wherein the illuminating device comprises a light-emitting diode.

31. An apparatus for electromagnetically affecting a particle of interest in a specimen, comprising
   (a) a stage capable of supporting the specimen;
   (b) a detector capable of resolving a particle of interest within the specimen, wherein the detector comprises a plurality of cameras, each camera viewing a different focal planar region, each of the viewed focal planar regions producing a different sectional image of the specimen;
   (c) a means for locating the particle of interest in three dimensions;
   (d) a means for focusing electromagnetic radiation to a focal volume within the specimen; and
   (e) a means for adjusting the relative positions of the stage and electromagnetic radiation focusing means, thereby positioning the particle of interest within the focal volume.

32. The apparatus of claim 31, wherein at least one of the cameras views a depth of field of less than 100 microns.

33. The apparatus of claim 31, wherein the different sectional images are produced by focusing the cameras on different sections of the specimen.

34. The apparatus of claim 33, wherein the distance between the midplanes of adjacent focal planar regions is about the depths of field that are viewed by the cameras.

35. The apparatus of claim 31, wherein the focal planar regions are substantially non-overlapping in the Z-level.

36. The apparatus of claim 31, wherein the cameras have directions of view that are substantially parallel to one another.

37. The apparatus of claim 31, wherein the apparatus is capable of electromagnetically affecting particles in at least 10 separate focal volumes in the specimen per minute.

38. The apparatus of claim 31, wherein the means for locating the particle comprises a device for processing more than one two-dimensional representations to produce a three-dimensional representation.

39. The apparatus of claim 31, wherein the adjusting means comprises an automated positioning device functionally connected to the electromagnetic radiation focusing means.

40. The apparatus of claim 31, wherein the adjusting means comprises an automated positioning device functionally connected to the stage.

41. The apparatus of claim 31, wherein the adjusting means comprises an automated positioning device functionally connected to the electromagnetic radiation focusing means and stage.

42. The apparatus of claim 31, further comprising an electromagnetic radiation source directed to the electromagnetic radiation focusing means.

43. The apparatus of claim 42, wherein the electromagnetic radiation source is at least one laser.

44. The apparatus of claim 43, wherein the radiation is convergent.

45. The apparatus of claim 43, wherein the at least one laser emits a wavelength between 100 nanometers and 30 micrometers.

46. The apparatus of claim 42, wherein the source comprises a plurality of lasers.

47. The apparatus of claim 46, wherein the radiation beams from the lasers intersect in the focal volume.

48. The apparatus of claim 46, wherein the lasers emit radiation of differing wavelengths.

49. The apparatus of claim 31, whereby the focal volume can comprise sufficient energy to kill a cell.

50. The apparatus of claim 31, whereby the focal volume can comprise sufficient energy to optoinject a cell.

51. The apparatus of claim 31, whereby the focal volume can comprise sufficient energy to inactivate a cell component.

52. The apparatus of claim 31, whereby the focal volume can comprise sufficient energy to activate a photosensitive agent.

53. The apparatus of claim 52, wherein the photosensitive agent is a caged compound, photodynamic therapy agent or fluorophore.

54. The apparatus of claim 31, further comprising an illuminating device placed to illuminate the specimen.

55. The apparatus of claim 54, wherein the illuminating device comprises a lamp.

56. The apparatus of claim 54, wherein the illuminating device comprises a laser.

57. The apparatus of claim 54, wherein the illuminating device comprises a light-emitting diode.

58. An apparatus for electromagnetically affecting a particle of interest in a specimen, comprising
  (a) a stage capable of supporting the specimen;
  (b) a detector capable of resolving a particle of interest within the specimen, wherein the detector comprises a camera viewing a shallow focal planar region and wherein the focal planar region can be refocused on different sections of the specimen;
  (c) a means for locating the particle of interest in three dimensions;
  (d) a means for focusing electromagnetic radiation to a focal volume within the specimen; and
  (e) a means for adjusting the relative positions of the stage and electromagnetic radiation focusing means, thereby positioning the particle of interest within the focal volume.

59. The apparatus of claim 58, wherein the focal planar region is refocused on different sections of the specimen at different points in time.

60. The apparatus of claim 59, wherein refocusing occurs at a rate of at least 1 Hz.

61. The apparatus of claim 58, wherein the refocusing is automated.

62. The apparatus of claim 58, wherein the detector is capable of obtaining a plurality of non-identical two-dimensional images, wherein a particle of interest is discernable in at least one of the two-dimensional images.

63. The apparatus of claim 58, wherein the apparatus is capable of electromagnetically affecting particles in at least 10 separate focal volumes in the specimen per minute.

64. The apparatus of claim 58, wherein the detector comprises a plurality of cameras capable of imaging the specimen from different directions of view.

65. The apparatus of claim 58, wherein the means for locating the particle comprises a device for processing more than one two-dimensional representations to produce a three-dimensional representation.

66. The apparatus of claim 58, wherein the adjusting means comprises an automated positioning device functionally connected to the electromagnetic radiation focusing means.

67. The apparatus of claim 58, wherein the adjusting means comprises an automated positioning device functionally connected to the stage.

68. The apparatus of claim 58, wherein the adjusting means comprises an automated positioning device functionally connected to the electromagnetic radiation focusing means and stage.

69. The apparatus of claim 58, further comprising an electromagnetic radiation source directed to the electromagnetic radiation focusing means.

70. The apparatus of claim 69, wherein the electromagnetic radiation source is at least one laser.

71. The apparatus of claim 70, wherein the radiation is convergent.

72. The apparatus of claim 70, wherein the at least one laser emits a wavelength between 100 nanometers and 30 micrometers.

73. The apparatus of claim 69, wherein the source comprises a plurality of lasers.

74. The apparatus of claim 73, wherein the radiation beams from the lasers intersect in the focal volume.

75. The apparatus of claim 73, wherein the lasers emit radiation of differing wavelengths.

76. The apparatus of claim 58, whereby the focal volume can comprise sufficient energy to kill a cell.

77. The apparatus of claim 58, whereby the focal volume can comprise sufficient energy to optoinject a cell.

78. The apparatus of claim 58, whereby the focal volume can comprise sufficient energy to inactivate a cell component.

79. The apparatus of claim 58, whereby the focal volume can comprise sufficient energy to activate a photosensitive agent.

80. The apparatus of claim 79, wherein the photosensitive agent is a caged compound, photodynamic therapy agent or fluorophore.

81. The apparatus of claim 58, further comprising an illuminating device placed to illuminate the specimen.

82. The apparatus of claim 81, wherein the illuminating device comprises a lamp.

83. The apparatus of claim 81, wherein the illuminating device comprises a laser.

84. The apparatus of claim 81, wherein the illuminating device comprises a light-emitting diode.

85. An apparatus for electromagnetically affecting a particle of interest in a specimen, comprising
  (a) a stage capable of supporting the specimen;
  (b) a detector capable of resolving a particle of interest within the specimen, wherein the detector comprises a camera viewing a shallow depth of field and wherein the detector can be automatically refocused to obtain different sectional images of the specimen;
  (c) a means for locating the particle of interest in three dimensions;
  (d) a means for focusing electromagnetic radiation to a focal volume within the specimen; and
  (e) a means for adjusting the relative positions of the stage and electromagnetic radiation focusing means, thereby positioning the particle of interest within the focal volume.

86. The apparatus of claim 85, wherein the automatic refocus comprises moving the camera.

87. The apparatus of claim 85, wherein the camera views a shallow depth of field through a lens and the automatic refocus comprises moving the lens.

88. The apparatus of claim 85, wherein the camera views a shallow depth of field reflected by a mirror and the automatic refocus comprises moving the mirror.

89. The apparatus of claim 85, wherein the automatic refocus comprises moving the specimen.

90. The apparatus of claim 85, wherein the apparatus is capable of electromagnetically affecting particles in at least 10 separate focal volumes in the specimen per minute.

91. The apparatus of claim 85, wherein the detector comprises a plurality of cameras capable of imaging the specimen from different directions of view.

92. The apparatus of claim 85, wherein the means for locating the particle comprises a device for processing more than one two-dimensional representations to produce a three-dimensional representation.

93. The apparatus of claim 85, wherein the adjusting means comprises an automated positioning device functionally connected to the electromagnetic radiation focusing means.

94. The apparatus of claim 85, wherein the adjusting means comprises an automated positioning device functionally connected to the stage.

95. The apparatus of claim 85, wherein the adjusting means comprises an automated positioning device functionally connected to the electromagnetic radiation focusing means and stage.

96. The apparatus of claim 85, further comprising an electromagnetic radiation source directed to the electromagnetic radiation focusing means.

97. The apparatus of claim 96, wherein the electromagnetic radiation source is at least one laser.

98. The apparatus of claim 97, wherein the at least one laser emits a wavelength between 100 nanometers and 30 micrometers.

99. The apparatus of claim 96, wherein the radiation is convergent.

100. The apparatus of claim 96, wherein the source comprises a plurality of lasers.

101. The apparatus of claim 100, wherein the radiation beams from the lasers intersect in the focal volume.

102. The apparatus of claim 100, wherein the lasers emit radiation of differing wavelengths.

103. The apparatus of claim 85, whereby the focal volume can comprise sufficient energy to kill a cell.

104. The apparatus of claim 85, whereby the focal volume can comprise sufficient energy to optoinject a cell.

105. The apparatus of claim 85, whereby the focal volume can comprise sufficient energy to inactivate a cell component.

106. The apparatus of claim 85, whereby the focal volume can comprise sufficient energy to activate a photosensitive agent.

107. The apparatus of claim 106, wherein the photosensitive agent is a caged compound, photodynamic therapy agent or fluorophore.

108. The apparatus of claim 85, further comprising an illuminating device placed to illuminate the specimen.

109. The apparatus of claim 108, wherein the illuminating device comprises a lamp.

110. The apparatus of claim 108, wherein the illuminating device comprises a laser.

111. The apparatus of claim 108, wherein the illuminating device comprises a light-emitting diode.

112. A method for electromagnetically affecting a particle of interest in a specimen, comprising the steps of
 (a) obtaining a plurality of nonidentical two-dimensional sectional representations of the specimen in which the particle of interest is discernable in at least one of the sectional representations;
 (b) combining the plurality of sectional two-dimensional representations to produce a three-dimensional representation of the specimen;
 (c) locating the particle of interest in three dimensions based on the three-dimensional representation; and
 (d) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

113. The method of claim 112, wherein the specimen is a multilayer of particles.

114. The method of claim 112, wherein the specimen is a biological specimen.

115. The method of claim 114, wherein the particle is a cell.

116. The method of claim 115, wherein the electromagnetic effect is death.

117. The method of claim 115, wherein the electromagnetic effect is optoinjection.

118. The method of claim 115, wherein the electromagnetic effect is alteration of gene expression.

119. The method of claim 115, wherein the electromagnetic effect is fluorescence.

120. The method of claim 115, wherein the electromagnetic effect is uncaging of an ion.

121. The method of claim 112, wherein the particle of interest is discernable by the presence of a selective marker.

122. The method of claim 121, wherein the selective marker is nondestructive to the particle.

123. The method of claim 121, wherein the selective marker comprises a dye.

124. The method of claim 121, wherein the selective marker comprises an antibody.

125. The method of claim 121, wherein the marker is selective for tumor cells.

126. The method of claim 112, wherein the particle of interest is discernable by a plurality of selective markers.

127. The method of claim 112, wherein the particle of interest is discernable by the absence of a selective marker.

128. The method of claim 112, wherein the position of the specimen is changed to intersect the portion of the specimen containing the particle of interest with the focal volume.

129. The method of claim 112, wherein the position of the focal volume is changed to intersect the portion of the specimen containing the particle of interest with the focal volume.

130. The method of claim 112, wherein at least 10 separate portions of the specimen containing a located particle are electromagnetically affected per minute.

131. The method of claim 112, wherein at least 500,000 separate portions of the specimen containing a located particle are electromagnetically affected per minute.

132. The method of claim 112, wherein the plurality of representations is obtained with a plurality of cameras, each camera viewing a different focal planar region, each of the viewed focal planar regions producing a different sectional representation of the specimen.

133. The method of claim 132, wherein at least one of the cameras views a depth of field of less than 100 microns.

134. The method of claim 132, wherein the different sectional representations are produced by focusing the camera views to different focal planar regions in the specimen.

135. The method of claim 134, wherein the distance between the midplanes of adjacent focal planar regions is about the depths of field that are viewed by the cameras.

136. The method of claim 132, wherein the sectional representations are substantially non-overlapping.

137. The method of claim 132, wherein the directions-of-view of the cameras are substantially parallel to one another.

138. The method of claim 112, wherein the plurality of representations is obtained with a camera viewing a shallow depth of field and wherein the focal planar region can be refocused on different sections of the specimen.

139. The apparatus of claim 138, wherein the refocusing is automated.

140. The method of claim 112, wherein the plurality of representations is obtained with a detector viewing a shallow depth of field and wherein the detector can be automatically refocused to obtain different sectional representations of the specimen.

141. The method of claim 112, wherein the electromagnetic radiation is produced by at least one laser.

142. The method of claim 141, wherein the electromagnetic radiation comprises convergent rays.

143. The method of claim 141, wherein the electromagnetic radiation is between 100 nanometers and 30 micrometers.

144. The method of claim 112, wherein the electromagnetic radiation is produced by a plurality of lasers.

145. The method of claim 144, wherein the radiation beams from the lasers intersect in the focal volume.

146. The method of claim 144, wherein the lasers emit radiation of differing wavelengths.

147. The method of claim 112, wherein the specimen is illuminated.

148. The method of claim 147, wherein the specimen is illuminated with a lamp.

149. The method of claim 147, wherein the specimen is illuminated with a laser.

150. The method of claim 147, wherein the specimen is illuminated with a light-emitting diode.

151. A method for electromagnetically affecting a particle of interest in a specimen, comprising the steps of:
   (a) focusing a plurality of detectors on a plurality of focal planar regions in a specimen;
   (b) obtaining a plurality of two-dimensional sectional representations each corresponding to one of the focal planar regions, wherein a particle of interest can be discerned in at least one of the two-dimensional sectional representations;
   (c) storing the plurality of two-dimensional sectional representations in a computer memory;
   (d) combining the plurality of two-dimensional sectional representations to produce a three-dimensional representation of at least a portion of the specimen;
   (e) locating the particle of interest in the specimen based on the three-dimensional representation of at least a portion of the specimen; and
   (f) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

152. A method for electromagnetically affecting a particle of interest in a specimen, comprising the steps of:
   (a) obtaining a plurality of two-dimensional sectional representations of the specimen at different Z-levels, wherein the particle of interest is discernable in at least one of the sectional representations;
   (b) selecting a two-dimensional sectional representation from the plurality of two-dimensional sectional representations wherein the particle of interest is in focus;
   (c) locating the particle of interest in the specimen with reference to X and Y coordinates of the particle in the selected two-dimensional sectional representation and the Z-level of the selected two-dimensional sectional representation; and
   (d) focusing electromagnetic radiation to a focal volume, the focal volume intersecting a portion of the specimen containing the particle of interest, wherein the radiation within the focal volume substantially affects only the portion of the specimen within the focal volume, the portion of the specimen within the focal volume being surrounded by an envelope of substantially unaffected specimen.

* * * * *